United States Patent [19]

Brand et al.

[11] Patent Number: 5,003,101

[45] Date of Patent: Mar. 26, 1991

[54] ACRYLATES AND FUNGICIDES CONTAINING THEM

[75] Inventors: Siegbert Brand, Weinheim; Franz Schuetz, Ludwigshafen; Bernd Wenderoth, Lampertheim; Hubert Sauter, Mannheim; Eberhard Ammermann, Ludwigshafen; Gissela Lorenz, Neustadt, all of Fed. Rep. of Germany

[73] Assignee: BASF Aktiengesellschaft, Ludwigshafen, Fed. Rep. of Germany

[21] Appl. No.: 347,656

[22] Filed: May 5, 1989

[30] Foreign Application Priority Data

May 14, 1988 [DE] Fed. Rep. of Germany ....... 3816577

[51] Int. Cl.$^5$ ..................... C07C 69/76; A01N 37/10
[52] U.S. Cl. ..................... 560/104; 560/15; 560/55; 558/412; 558/423; 558/426
[58] Field of Search ..................... 560/104, 15, 55; 558/412, 423; 514/532, 538, 543

[56] References Cited

U.S. PATENT DOCUMENTS

| | | | |
|---|---|---|---|
| 3,622,569 | 11/1971 | Lemieux | 540/328 |
| 4,178,460 | 12/1979 | Berkelhammer et al. | 562/426 |
| 4,199,595 | 4/1980 | Berkelhammer et al. | 424/304 |
| 4,239,777 | 12/1980 | Berkelhammer et al. | 424/304 |
| 4,709,078 | 5/1986 | Schriner et al. | 562/426 |
| 4,723,034 | 5/1986 | Schriner et al. | 424/304 |
| 4,782,177 | 2/1987 | Lausberg | 424/304 |

FOREIGN PATENT DOCUMENTS 178826 4/1986 European Pat. Off.
260832 3/1988 European Pat. Off.

OTHER PUBLICATIONS

CA 112(7) 55007n, 1989.
CA 90(23):186606p, 1979.
CA 106(7) 50525, 1986.
Chemical Abstracts, vol. 95, #168044c (1981).
Journal of Organic Chemistry, vol. 53, pp. 607-610 (1988).

Primary Examiner—Paul J. Killos

Attorney, Agent, or Firm—Oblon, Spivak, McClelland, Maier & Neustadt

[57] ABSTRACT

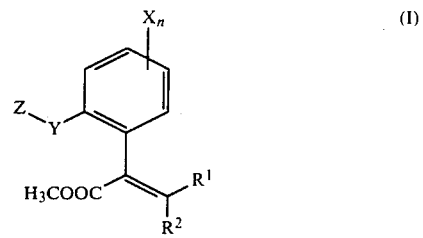

where
$R^1$ and $R^2$ are halogen or oxiranyl, or alkyl, alkoxy or alkylthio, or $R^1$ and $R^2$ together denote a saturated or unsaturated 3- to 6-membered ring whcih may contain from 1 to 3 heteroatoms and which is unsubstituted or substituted, and
X is hydrogen, halogen, cyano, nitro, substituted or unsubstituted alkyl, substituted or unsubstituted alkoxy, substituted or unsubstituted haloalkyl,
n is 1, 2, 3 or 4,
Y is substituted or unsubstituted alkylene, alkenylene, alkynylene, O, S(O), unsubstituted or alkyl-substituted N, oxycarbonyl, carbonyloxy, carbonyloxyalkylene, oxycarbonylalkylene, oxyalkylene, thioalkylene, azo, carbonylamino, aminocarbonyl,

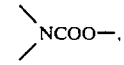

methylenoxy or methylenethio and
Z is hydrogen, alkyl, cycloalkyl, aryl, aralkyl, aralkenyl, aralkoxy, aryloxy, aryloxyalkyl, hetaryl, alkoxy, alkoxyalkyl, alkylthio, or haloalkyl, these radicals being unsubstituted or substituted by halogen, cyano, nitro, alkyl, alkenyl, haloalkenyl, alkoxy, haloalkyl, alkoxycarbonyl or unsubstituted or substituted phenyl,
and fungicides containing these compounds.

4 Claims, No Drawings

ACRYLATES AND FUNGICIDES CONTAINING THEM

The present invention relates to novel acrylates, fungicides containing them and their use as fungicides.

It is known that N-tridecyl-2,6-dimethylmorpholine or its salts, for example the acetate, can be used as fungicides (DE-1 164 152 and DE-1 173 722). It is also known that methyl α-phenyl-β-methoxyacrylate derivatives (DE-3 519 282.8) can be used as fungicides.

However, their action is insufficient in some cases.

We have found that novel acrylates of the formula

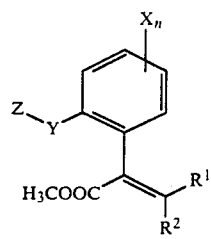

where $R^1$ and $R^2$ are identical or different and are each halogen, $C_1$-$C_4$-alkyl, $C_1$-$C_3$-alkoxy, $C_1$-$C_3$-alkylthio, oxiranyl which is unsubstituted or substituted by halogen, hydroxyl, $C_1$-$C_3$-alkoxy, $C_1$-$C_3$-haloalkyl or $C_1$-$C_3$-haloalkoxy, or $R^1$ and $R^2$ together form an unsaturated or saturated 3-membered to 6-membered ring which may contain 1 to 3 heteroatoms O or $S(O)_m$ (where m is 0, 1 or 2) and is unsubstituted or substituted by halogen, hydroxyl, $C_1$-$C_3$-alkyl, $C_1$-$C_3$-alkoxy, $C_1$-$C_3$-haloalkyl or oxo, the radicals X are identical or different and are each hydrogen, halogen, cyano, nitro, unsubstituted or substituted $C_1$-$C_4$-alkyl, unsubstituted or substituted $C_1$-$C_4$-alkoxy, or unsubstituted or substituted halo-$C_1$-$C_4$-alkyl, n is from 1 to 4, Y is unsubstituted or substituted $C_1$-$C_4$-alkylene, alkylene, $C_2$-$C_4$-alkenylene, $C_2$-$C_4$-alkynylene, O, $S(O)_p$ (where p is 0, 1 or 2), unsubstituted or $C_1$-$C_4$-alkyl-substituted N, oxycarbonyl, carbonyloxy, carbonyloxy-$C_1$-$C_4$-alkylene, oxycarbonyl-$C_1$-$C_4$-alkylene, oxy-$C_1$-$C_4$-alkylene, thio-$C_1$-$C_4$-alkylene, azo, carbonylamino, aminocarbonyl,

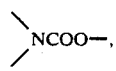

methyleneoxy or methylenethio, and Z is hydrogen, a cycloalkyl, aryl, arylalkyl, aralkenyl, aralkoxy, aryloxy, aryloxyalkyl, hetaryl, alkoxy, alkoxyalkyl, alkylthio or haloalkyl, these radicals being unsubstituted or substituted by halogen, cyano, nitro, alkyl, alkenyl, haloalkenyl, alkoxy, haloalkyl, unsubstituted or substituted phenyl or alkoxycarbonyl, have a very good fungicidal action.

The novel compounds of the formula I may be obtained in the preparation in the form of mixtures of stereoisomers (E,Z-isomers, diastereomers or enantiomers), which can be separated into the individual components in a conventional manner, for example by crystallization or chromatography. Both the individual isomers and their mixtures can be used as fungicides and form the subject of the invention.

$R^1$ and $R^2$ are identical or different and are each preferably methyl, ethyl, n-propyl, isopropyl, fluorine, chlorine, bromine,

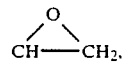

$OCH_3$, $OC_2H_5$, $CH_2OCH_3$, $SCH_3$, $SCH_2H_5$ or $CF_3$, or $R^1$ and $R^2$ together are preferably —$(CH_2)_q$— (where q is 3, 4 or 5), —CH=CH—CH=CH—, $O(CH_2)_2O$—, —$O(CH_2)_3O$—, —$OCH_2C(CH_3)_2CH_2O$—, —$S(CH_2)_2S$—, —$S(CH_2)_3S$—,

or —$CH_2(CH_2)_2)_2$—.

n is preferably zero.

Y is preferably methylene, ethylene, ethenylene, ethynylene, O, S, methyleneoxy, oxymethylene, carbonyloxy, oxycarbonyl or

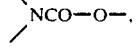

and Z is preferably hydrogen, $C_1$-$C_{16}$-alkyl, $C_2$-$C_{16}$-alkenyl, $C_2$-$C_{16}$-alkynyl (e.g. methyl, ethyl, n-propyl, isopropyl, n-butyl, tert-butyl, 2,2-dimethylpropyl, 2-ethylhex-1-yl, 2,6-dimethylhept-1-yl, 2,6,10-trimethylundec-yl, allyl, prenyl, geranyl, 2,3-dihydrogeranyl, tetrahydrogeranyl, 2,6-dimethylhepta-1,5-dien-1yl, 2,6-dimethylhept-5-en-1-yl or 2-ethylhex-1-en-1-yl), which are unsubstituted or substituted by $C_1$-$C_4$-alkoxy or halogen, or Z is furthermore preferably $C_3$-$C_{12}$-cycloalkyl which is substituted by $C_1$-$C_4$-alkyl, halogen or $C_1$-$C_4$-alkoxy (e.g. cyclohexyl, cyclopropyl, in particular 1-methylcyclopropyl, 2-methylcyclopropyl or 2-dichlorocyclopropyl or 2,2-dichloro-1-methylcyclopropyl (A1), 2,2-dichloro-3,3-dimethylcyclopropyl (A2), 2,2,3,3-tetramethylcyclopropyl (A3), 2-(2'-methyl-1'-propenyl)-3,3-dimethylcyclopropyl (A4), 2-(2',2'-difluorovinyl)-3,3-dimethylcyclopropyl (A5), 2-(2',2'-dichlorovinyl)-3,3-dimethylcyclopropyl (A6), 2-(2',2'-dibromovinyl)-3,3-dimethylcyclopropyl (A7), 2-phenylcyclopropyl (A8), 2-(4-chlorophenyl)-cyclopropyl (A9), 2,2-dichloro-3-phenylcyclopropyl (A10) or 2-carbomethoxycyclopropyl (A11)), or is furthermore preferably aryl, in particular phenyl, phenoxyphenyl, phenylphenyl, $C_1$-$C_4$-alkoxyphenyl, trifluoromethylphenyl, halophenyl or $C_1$-$C_4$-alkylphenyl (e.g. 2-fluoro-, 3-fluoro-, 4-fluoro-, 2-chloro-, 3-chloro-, 4-chloro-, 6-fluoro-, 2,4-dichloro-, 2,6-dichloro-, 3,5-dichloro-, 2,4,6-trichloro-, 2-bromo-, 4-bromo-, 2-methyl-3-methyl-, 4-methyl-, 2,4-dimethyl-, 2,6-dimethyl-, 2,4,6-trimethyl-, 4-tert-butyl-, 2-methoxy-, 3-methoxy-, 4-methoxy-, 2,3-dimethoxy-, 2-$CF_3$-, 3-$CF_3$, 4-$CF_3$-, 3-tert-butoxy-, 4-tert-butoxy-, 4-phenoxy-, 4p-henylphenyl or naphthyl (1- or 2-naphthyl)), aryloxy (e.g. phenoxy), aralkyl, phenyl-$C_1$-$C_4$-alkyl (e.g. benzyl, halobenzyl, $C_1$-$C_4$-alkylbenzyl, 2-chlorobenzyl, 2-methylbenzyl, 2-phenylethyl, 3-phenylpropyl or 4-phenylbutyl), aralkenyl (e.g. styryl, halostyryl, $C_1$-$C_4$-alkylstyryl, ortho-chlorostyryl or para-tert-butylstyryl), hetaryl having 5 or 6 ring members and nitrogen, oxygen or sulfur as heteroatoms (e.g. 2-pyridyl-, 2-pyrimidyl-, 2-furyl- or 2-thiophenyl-), aryloxy-$C_1$-$C_4$-alkyl (e.g. phenoxyethyl or 4-phenoxybutyl), halo-$C_1$-$C_4$-alkyl (e.g. trifluoromethyl or trichloromethyl), halo-$C_1$-$C_4$-alkoxy, (e.g. trifluoromethoxy or trichloromethoxy).

The compounds of the formula I can be prepared, for example, by the reactions shown in scheme 1.

Grignard compounds VI are reacted with imidazolides of the formula VII (J. S. Nimitz and H. S. Mosher, J. Org. Chem. 46 (1981), 211), the radicals $X_n$, Y, Z and R having the abovementioned meanings.

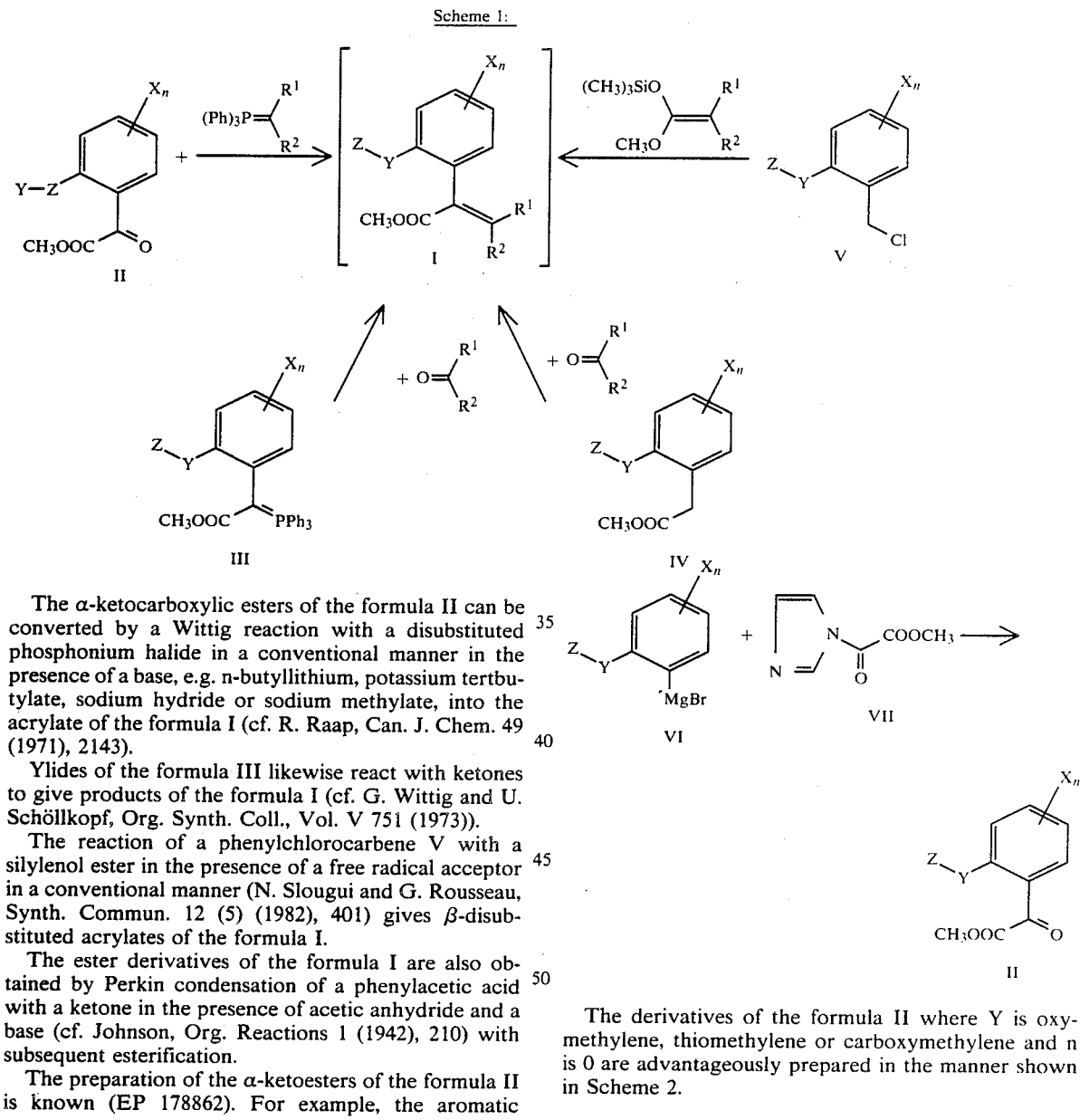

Scheme 1

The α-ketocarboxylic esters of the formula II can be converted by a Wittig reaction with a disubstituted phosphonium halide in a conventional manner in the presence of a base, e.g. n-butyllithium, potassium tertbutylate, sodium hydride or sodium methylate, into the acrylate of the formula I (cf. R. Raap, Can. J. Chem. 49 (1971), 2143).

Ylides of the formula III likewise react with ketones to give products of the formula I (cf. G. Wittig and U. Schöllkopf, Org. Synth. Coll., Vol. V 751 (1973)).

The reaction of a phenylchlorocarbene V with a silylenol ester in the presence of a free radical acceptor in a conventional manner (N. Slougui and G. Rousseau, Synth. Commun. 12 (5) (1982), 401) gives β-disubstituted acrylates of the formula I.

The ester derivatives of the formula I are also obtained by Perkin condensation of a phenylacetic acid with a ketone in the presence of acetic anhydride and a base (cf. Johnson, Org. Reactions 1 (1942), 210) with subsequent esterification.

The preparation of the α-ketoesters of the formula II is known (EP 178862). For example, the aromatic The derivatives of the formula II where Y is oxymethylene, thiomethylene or carboxymethylene and n is 0 are advantageously prepared in the manner shown in Scheme 2.

Scheme 2

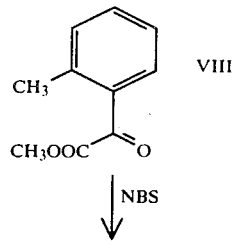

Scheme 2

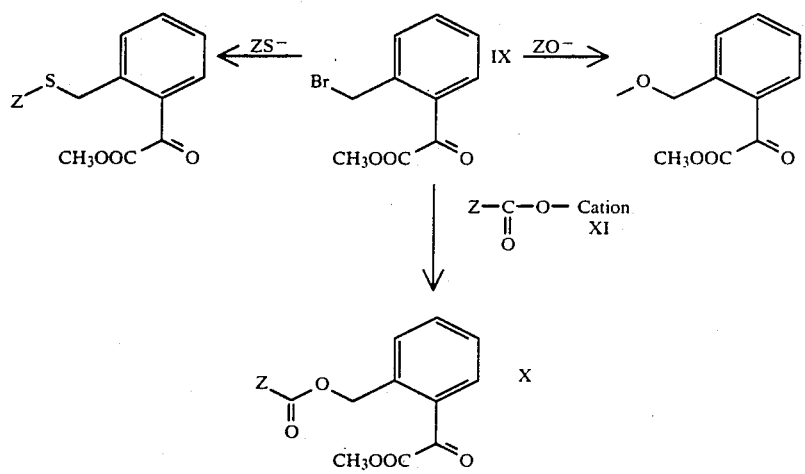

α-Ketoesters of the formula VIII can be converted into the benzyl bromides of the formula IX with bromine or N-bromosuccinimide (NBS) in, for example, tetrachloromethane, if necessary with exposure to a light source of suitable wavelength (e.g. Hg vapor lamp, 300 watt) (cf. Horner and Winkelmann, Angew. Chem. 71 (1959), 349).

The novel α-ketocarboxylic esters of the formula IX are useful intermediates. They can be converted, for example, into the derivatives of the formula X by reacting them with an alkali metal salt, alkaline earth metal salt or ammonium salt of a carboxylic acid of the formula XI, where Z has the abovementioned meanings, in a solvent or diluent, e.g. acetone, acetonitrile, dimethyl sulfoxide, dioxan, dimethylformamide, N-methylpyrrolidone, N,N'-dimethylpropyleneurea or pyridine, with or without the addition of a catalyst, for example 0.01–10% by weight, based on composition X, of tetramethylethylenediamine or potassium iodide.

The acrylate derivates of the general formula XII can be prepared by the reactions shown in Scheme 3.

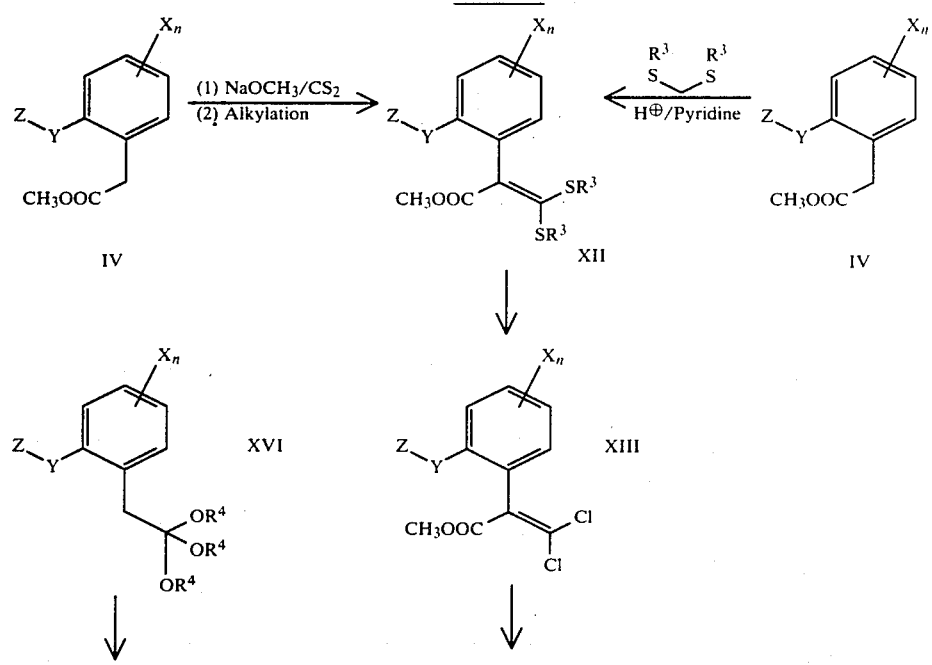

Scheme 3

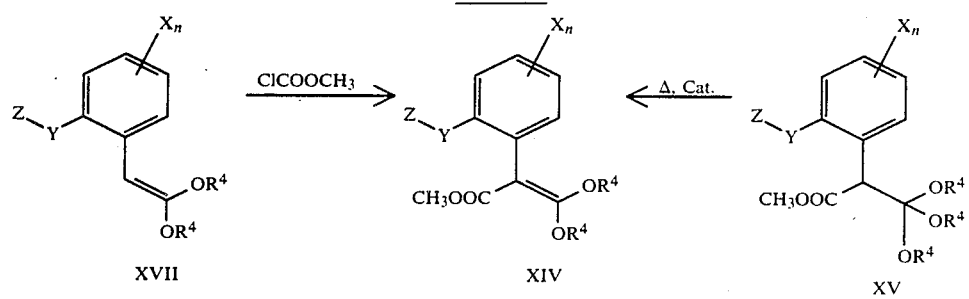

(R[3] and R[4] are each alkyl or alkylene; see Table 3)

Ketene mercaptals of the formula XII can be prepared by alkylation of the dithiocarboxylic acid salts obtainable from phenylacetic esters (IV) and carbon disulfide (cf. R. Gompper and W. Töpfl, Chem. Ber. 95 (1962), 2861, and Ann. Chem. 659 (1962), 90) or by reacting trithiocarbonates with active methylene components (cf. R. Gompper and E. Kutter, Chem. Ber. 98 (1965), 1365).

They are converted into the $\beta,\beta$-dichloroacrylates of the formula XIII using phosphorus pentachloride (cf. R. Gompper et al., Angew. Chem. 76 (1964), 583).

The conversion of these activated dichloromethylenes into the ketene acetals of the formula XIV is achieved by reaction with an alcoholate (cf. S. M. McElvain and H. F. McShane, J. Amer. Chem. Soc. 74 (1952), 2662).

Another method of obtaining the $\beta,\beta$-dialkoxyacrylates of the formula XIV is the base-catalyzed elimination of alcohol from the orthocarboxylic triesters of the formula XV or XVI (cf. S. M. McElvain et al., J. Amer. Chem. Soc. 73 (1951), 206, ibid, 71 (1949), 47); in the case of arylketene acetals (XVII) acylation with methyl chloroformate is subsequently carried out (cf. S. M. McElvain and R. D. Mullineaux, J. Amer. Chem. Soc. 74 (1952), 1811).

The Examples which follow illustrate the preparation of the novel compounds of the formula I:

1. Preparation of methyl 3-methyl-2-[2'-($\alpha$-methylcyclopropylcarboxymethylene)-phenyl]-2-butenoate (No. 280, Table 1)

(a) Preparation of methyl orthobromoethylphenylglyoxylate 50.0 g (0.28 mole) of methyl orthomethylphenylglyoxylate are dissolved together with 50.0 g (0.28 mole) of freshly crystallized N-bromosuccinimide in 3 l of carbon tetrachloride. The mixture is exposed to a 300 W Hg vapor lamp for one hour, the reaction mixture is evaporated down to about 1 l and the organic phase is washed with 3×200 ml of water. The organic phase is dried over sodium sulfate and the solvent is distilled off, after which the residue is chromatographed over silica gel using 1:9 methyl tert-butyl ether/hexane to give 10 g of ketoester (II, YZ=CH$_3$), and 21.1 g of benzyl bromide (II, YZ=CH$_2$Br) (37%, based on converted ketoester) as a yellow oil.

$1_H$ (CDCl$_3$)$\delta$=3.97(s,3H), 4.90(s,2H), 7.4–7.8(m,4H).
IR (Film): 2955; 1740, 1690; 1435, 1318, 1207, 999 cm$^{-1}$.

(b) Preparation of methyl ortho-($\alpha$-methylcyclopropylcarboxymethylene)-phenylglyoxylate 13.8 g (0.1 mole) of the potassium salt of $\alpha$-methylcyclopropanecarboxylic acid are dissolved together with 21.1 g (0.082 mole) of ortho-(bromomethyl)-phenylglyoxylic acid and 0.3 g of potassium iodide in 300 ml of N-methylpyrrolidone. The mixture is stirred for 15 hours at 23° C., poured onto 300 ml of ice water and extracted with 3×200 ml of methyl tert-butyl ether. The organic phases are washed with water, dried with sodium sulfate and evaporated down to give 24.0 g (106%) of chromatographically pure ester, which is used in the subsequent reaction.

$1_H$(CDCl$_3$): $\delta$=0.70(m,2H), 1.27(m,2H), 1.35(s,3H), 3.96(s,3H), 5.46(s,2H), 7.4–7.8(m,4H).

(c) Preparation of methyl 3-methyl-2-[2'-($\alpha$-methylcyclopropylcarboxymethylene)-phenyl]-2-butenoate (No. 280, Table 1)

13.8 g (0.032 mole) of isopropyltriphenylphosphonium iodide in 100 ml of anhydrous tetrahydrofuran are initially taken under nitrogen. 20 ml of a 1.6 molar solution of n-butyllithium in hexane are added dropwise at 0° C. After 1 hour at 0° C., 8.0 g (0.029 mole) of methyl ortho-($\alpha$-methylcyclopropylcarboxymethylene)-phenylglyoxylate dissolved in 40 ml of anhydrous tetrahydrofuran are added dropwise. The mixture is allowed to warm to 23° C. and is stirred for a further 2 hours, poured onto saturated ammonium chloride solution and extracted with methyl tert-butyl ether. The organic phases are washed with water, dried over sodium sulfate and evaporated down. The crude product is separated by column chromatography over silica gel using 1:9 methyl tert-butyl ether/hexane. 1.9 g (22%) of the abovementioned ester are obtained as an oil.

$1_H$(CDCl$_3$): $\delta$=0.65(m,2H), 1.25(m,2H), 1.30(s,3H), 1.60(s,3H), 2.25(s,3H), 3.65(s,3H), 5.00(s,2H), 7.0–7.5(m,4H).
(Film): 1720, 1630, 1322, 1222, 1156, 1090, 755 cm$^{-2}$.

Preparation of methyl 3-methyl-2-[2'-(2''-methylbenzyloxy-phenyl]-2-butenoate (No. 73, Table 1)

8.64 g (20 millimoles) of isopropylphosphonium iodide in 50 ml of anhydrous tetrahydrofuran are initially taken at 0° C. under nitrogen. 8.3 ml of 2.5 M n-butyllithium solution in hexane are added dropwise at 0° C. After 30 minutes at this temperature, 5.8 g (20 millimoles) of methyl 2-(2'-methylbenzyloxy)-phenylglyoxylate in 15 ml of anhydrous tetrahydrofuran are added all at once. Stirring is continued for 15 hours at room temperature (23° C.), the mixture is evaporated down in a rotary evaporator and the residue is partitioned between saturated ammonium chloride solution and 1:1 methyl tert-butyl ether/hexane. Extraction of the aqueous phase 3 times with this solvent mixture, drying of the organic phases over sodium sulfate and evaporation give a crude product, which is separated by column chromatography over silica gel using 1:2 methyl tert-butyl ether/hexane. 3.3 g (53%) of the abovementioned ester are obtained as a pale yellow oil.

$^1$H-NMR (CDCl$_3$): δ=1.67(s,3H), 2.22(s,3H), 2.40 (s,3H), 3.57(s,3H), 5.05 (s,3H), 6.9–7.4(m,8H).

IR (Film): 1714, 1600, 1490, 1449, 1302, 1270, 1224, 1088, 752 cm$^{-1}$

The compounds listed in the Tables below can be prepared in a similar manner.

TABLE 1

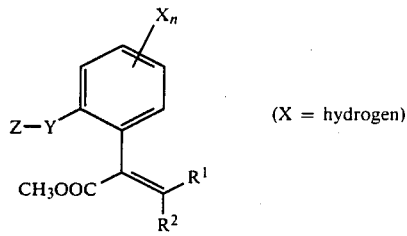

(X = hydrogen)

| No. | R$^1$ | R$^2$ | Y | Z | Data |
|---|---|---|---|---|---|
| 1 | CH$_3$ | CH$_3$ | CH$_2$CH$_2$ | C$_6$H$_5$ | |
| 2 | CH$_3$ | CH$_3$ | CH$_2$CH$_2$ | 2-F—C$_6$H$_4$ | |
| 3 | CH$_3$ | CH$_3$ | CH$_2$CH$_2$ | 3-F—C$_6$H$_4$ | |
| 4 | CH$_3$ | CH$_3$ | CH$_2$CH$_2$ | 4-F—C$_6$H$_4$ | |
| 5 | CH$_3$ | CH$_3$ | CH$_2$CH$_2$ | 2-Cl—C$_6$H$_4$ | |
| 6 | CH$_3$ | CH$_3$ | CH$_2$CH$_2$ | 3-Cl—C$_6$H$_4$ | |
| 7 | CH$_3$ | CH$_3$ | CH$_2$CH$_2$ | 4-Cl—C$_6$H$_4$ | |
| 8 | CH$_3$ | CH$_3$ | CH$_2$CH$_2$ | 2Cl,6F—C$_6$H$_3$ | |
| 9 | CH$_3$ | CH$_3$ | CH$_2$CH$_2$ | 2,4-Cl$_2$—C$_6$H$_3$ | |
| 10 | CH$_3$ | CH$_3$ | CH$_2$CH$_2$ | 2,6-Cl$_2$—C$_6$H$_3$ | |
| 11 | CH$_3$ | CH$_3$ | CH$_2$CH$_2$ | 3,5-Cl$_2$—C$_6$H$_3$ | |
| 12 | CH$_3$ | CH$_3$ | CH$_2$CH$_2$ | 2,4,6-Cl$_3$—C$_6$H$_2$ | |
| 13 | CH$_3$ | CH$_3$ | CH$_2$CH$_2$ | 2-CH$_3$—C$_6$H$_4$ | |
| 14 | CH$_3$ | CH$_3$ | CH$_2$CH$_2$ | 3-CH$_3$—C$_6$H$_4$ | |
| 15 | CH$_3$ | CH$_3$ | CH$_2$CH$_2$ | 4-CH$_3$—C$_6$H$_4$ | |
| 16 | CH$_3$ | CH$_3$ | CH$_2$CH$_2$ | 4-t-C$_4$H$_9$—C$_6$H$_4$ | |
| 17 | CH$_3$ | CH$_3$ | CH$_2$CH$_2$ | 2,4-(CH$_3$)$_2$—C$_6$H$_3$ | |
| 18 | CH$_3$ | CH$_3$ | CH$_2$CH$_2$ | 2,6-(CH$_3$)$_2$—C$_6$H$_3$ | |
| 19 | CH$_3$ | CH$_3$ | CH$_2$CH$_2$ | 2,4,6-(CH$_3$)$_3$—C$_6$H$_2$ | |
| 20 | CH$_3$ | CH$_3$ | CH$_2$CH$_2$ | 2-OCH$_3$—C$_6$H$_4$ | |
| 21 | CH$_3$ | CH$_3$ | CH$_2$CH$_2$ | 3-OCH$_3$—C$_6$H$_4$ | |
| 22 | CH$_3$ | CH$_3$ | CH$_2$CH$_2$ | 4-OCH$_3$—C$_6$H$_4$ | |
| 23 | CH$_3$ | CH$_3$ | CH$_2$CH$_2$ | 2-CF$_3$—C$_6$H$_4$ | |
| 24 | CH$_3$ | CH$_3$ | CH$_2$CH$_2$ | 3-CF$_3$—C$_6$H$_4$ | |
| 25 | CH$_3$ | CH$_3$ | CH$_2$CH$_2$ | 4-CF$_3$—C$_6$H$_4$ | |
| 26 | CH$_3$ | CH$_3$ | CH$_2$CH$_2$ | 4-O-t-C$_4$H$_9$—C$_6$H$_4$ | |
| 27 | CH$_3$ | CH$_3$ | CH$_2$CH$_2$ | 4-O—C$_6$H$_5$—C$_6$H$_4$ | |
| 28 | CH$_3$ | CH$_3$ | CH$_2$CH$_2$ | 4-C$_6$H$_5$—C$_6$H$_4$ | |
| 29 | CH$_3$ | CH$_3$ | CH$_2$CH$_2$ | 2-Br—C$_6$H$_4$ | |
| 30 | CH$_3$ | CH$_3$ | CH$_2$CH$_2$ | 4-Br—C$_6$H$_4$ | |
| 31 | CH$_3$ | CH$_3$ | —CH=CH— | C$_6$H$_5$ | |
| 32 | CH$_3$ | CH$_3$ | —CH=CH— | 2-F—C$_6$H$_4$ | |
| 33 | CH$_3$ | CH$_3$ | —CH=CH— | 3-F—C$_6$H$_4$ | |
| 34 | CH$_3$ | CH$_3$ | —CH=CH— | 4-F—C$_6$H$_4$ | |
| 35 | CH$_3$ | CH$_3$ | —CH=CH— | 2-Cl—C$_6$H$_4$ | |
| 36 | CH$_3$ | CH$_3$ | —CH=CH— | 3-Cl—C$_6$H$_4$ | |
| 37 | CH$_3$ | CH$_3$ | —CH=CH— | 4-Cl—C$_6$H$_4$ | |
| 38 | CH$_3$ | CH$_3$ | —CH=CH— | 2Cl,6F—C$_6$H$_3$ | |
| 39 | CH$_3$ | CH$_3$ | —CH=CH— | 2,4-Cl$_2$—C$_6$H$_3$ | |
| 40 | CH$_3$ | CH$_3$ | —CH=CH— | 2,6-Cl$_2$—C$_6$H$_3$ | |
| 41 | CH$_3$ | CH$_3$ | —CH=CH— | 3,5-Cl$_2$—C$_6$H$_3$ | |
| 42 | CH$_3$ | CH$_3$ | —CH=CH— | 2,4,6-Cl$_3$—C$_6$H$_2$ | |
| 43 | CH$_3$ | CH$_3$ | —CH=CH— | 2-CH$_3$—C$_6$H$_4$ | |
| 44 | CH$_3$ | CH$_3$ | —CH=CH— | 3-CH$_3$—C$_6$H$_4$ | |
| 45 | CH$_3$ | CH$_3$ | —CH=CH— | 4-CH$_3$—C$_6$H$_4$ | |
| 46 | CH$_3$ | CH$_3$ | —CH=CH— | 4-t-C$_4$H$_9$—C$_6$H$_4$ | |
| 47 | CH$_3$ | CH$_3$ | —CH=CH— | 2,4-(CH$_3$)$_2$—C$_6$H$_3$ | |
| 48 | CH$_3$ | CH$_3$ | —CH=CH— | 2,6-(CH$_3$)$_2$—C$_6$H$_3$ | |
| 49 | CH$_3$ | CH$_3$ | —CH=CH— | 2,4,6-(CH$_3$)$_3$—C$_6$H$_2$ | |
| 50 | CH$_3$ | CH$_3$ | —CH=CH— | 2-OCH$_3$—C$_6$H$_4$ | |
| 51 | CH$_3$ | CH$_3$ | —CH=CH— | 3-OCH$_3$—C$_6$H$_4$ | |
| 52 | CH$_3$ | CH$_3$ | —CH=CH— | 4-OCH$_3$—C$_6$H$_4$ | |
| 53 | CH$_3$ | CH$_3$ | —CH=CH— | 2-CF$_3$—C$_6$H$_4$ | |
| 54 | CH$_3$ | CH$_3$ | —CH=CH— | 3-CF$_3$—C$_6$H$_4$ | |
| 55 | CH$_3$ | CH$_3$ | —CH=CH— | 4-CF$_3$—C$_6$H$_4$ | |
| 56 | CH$_3$ | CH$_3$ | —CH=CH— | 4-O-t-C$_4$H$_9$—C$_6$H$_4$ | |
| 57 | CH$_3$ | CH$_3$ | —CH=CH— | 4-O-C$_6$H$_5$—C$_6$H$_4$ | |
| 58 | CH$_3$ | CH$_3$ | —CH=CH— | 4-C$_6$H$_5$—C$_6$H$_4$ | |
| 59 | CH$_3$ | CH$_3$ | —CH=CH— | 2-Br—C$_6$H$_4$ | |

TABLE 1-continued

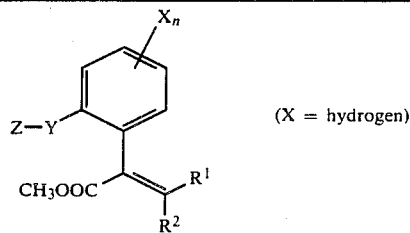

(X = hydrogen)

| No. | R¹ | R² | Y | Z | Data |
|---|---|---|---|---|---|
| 60 | $CH_3$ | $CH_3$ | —CH=CH— | 4-Br—$C_6H_4$ | |
| 61 | $CH_3$ | $CH_3$ | —$CH_2O$— | $C_6H_5$ | |
| 62 | $CH_3$ | $CH_3$ | —$CH_2O$— | 2-F—$C_6H_4$ | |
| 63 | $CH_3$ | $CH_3$ | —$CH_2O$— | 3-F—$C_6H_4$ | |
| 64 | $CH_3$ | $CH_3$ | —$CH_2O$— | 4-F—$C_6H_4$ | |
| 65 | $CH_3$ | $CH_3$ | —$CH_2O$— | 2-Cl—$C_6H_4$ | |
| 66 | $CH_3$ | $CH_3$ | —$CH_2O$— | 3-Cl—$C_6H_4$ | |
| 67 | $CH_3$ | $CH_3$ | —$CH_2O$— | 4-Cl—$C_6H_4$ | |
| 68 | $CH_3$ | $CH_3$ | —$CH_2O$— | 2Cl,6F—$C_6H_3$ | |
| 69 | $CH_3$ | $CH_3$ | —$CH_2O$— | 2,4-$Cl_2$—$C_6H_3$ | |
| 70 | $CH_3$ | $CH_3$ | —$CH_2O$— | 2,6-$Cl_2$—$C_6H_3$ | |
| 71 | $CH_3$ | $CH_3$ | —$CH_2O$— | 3,5-$Cl_2$—$C_6H_3$ | |
| 72 | $CH_3$ | $CH_3$ | —$CH_2O$— | 2,4,6-$Cl_3$—$C_6H_2$ | |
| 73 | $CH_3$ | $CH_3$ | —$CH_2O$— | 2-$CH_3$—$C_6H_4$ | oil; IR(film): 1713, 1630, 1276, 1215, 1112, 1092, 758, 708 |
| 74 | $CH_3$ | $CH_3$ | —$CH_2O$— | 3-$CH_3$—$C_6H_4$ | |
| 75 | $CH_3$ | $CH_3$ | —$CH_2O$— | 4-$CH_3$—$C_6H_4$ | |
| 76 | $CH_3$ | $CH_3$ | —$CH_2O$— | 4-t-$C_4H_9$—$C_6H_4$ | |
| 77 | $CH_3$ | $CH_3$ | —$CH_2O$— | 2,4-$(CH_3)_2$—$C_6H_3$ | |
| 78 | $CH_3$ | $CH_3$ | —$CH_2O$— | 2,6-$(CH_3)_2$—$C_6H_3$ | |
| 79 | $CH_3$ | $CH_3$ | —$CH_2O$— | 2,4,6-$(CH_3)_3$—$C_6H_2$ | |
| 80 | $CH_3$ | $CH_3$ | —$CH_2O$— | 2-$OCH_3$—$C_6H_4$ | |
| 81 | $CH_3$ | $CH_3$ | —$CH_2O$— | 3-$OCH_3$—$C_6H_4$ | |
| 82 | $CH_3$ | $CH_3$ | —$CH_2O$— | 4-$OCH_3$—$C_6H_4$ | |
| 83 | $CH_3$ | $CH_3$ | —$CH_2O$— | 2-$CF_3$—$C_6H_4$ | |
| 84 | $CH_3$ | $CH_3$ | —$CH_2O$— | 3-$CF_3$—$C_6H_4$ | |
| 85 | $CH_3$ | $CH_3$ | —$CH_2O$— | 4-$CF_3$—$C_6H_4$ | |
| 86 | $CH_3$ | $CH_3$ | —$CH_2O$— | 4-O-t-$C_4H_9$—$C_6H_4$ | |
| 87 | $CH_3$ | $CH_3$ | —$CH_2O$— | 4-O—$C_6H_5$—$C_6H_4$ | |
| 88 | $CH_3$ | $CH_3$ | —$CH_2O$— | 4-$C_6H_5$—$C_6H_4$ | |
| 89 | $CH_3$ | $CH_3$ | —$CH_2O$— | 2-Br—$C_6H_4$ | |
| 90 | $CH_3$ | $CH_3$ | —$CH_2O$— | 4-Br—$C_6H_4$ | |
| 91 | $CH_3$ | $CH_3$ | —$OCH_2$— | $C_6H_5$ | |
| 92 | $CH_3$ | $CH_3$ | —$OCH_2$— | 2-F—$C_6H_4$ | |
| 93 | $CH_3$ | $CH_3$ | —$OCH_2$— | 3-F—$C_6H_4$ | |
| 94 | $CH_3$ | $CH_3$ | —$OCH_2$— | 4-F—$C_6H_4$ | |
| 95 | $CH_3$ | $CH_3$ | —$OCH_2$— | 2-Cl—$C_6H_4$ | |
| 96 | $CH_3$ | $CH_3$ | —$OCH_2$— | 3-Cl—$C_6H_4$ | |
| 97 | $CH_3$ | $CH_3$ | —$OCH_2$— | 4-Cl—$C_6H_4$ | |
| 98 | $CH_3$ | $CH_3$ | —$OCH_2$— | 2Cl,6F—$C_6H_3$ | |
| 99 | $CH_3$ | $CH_3$ | —$OCH_2$— | 2,4-$Cl_2$—$C_6H_3$ | |
| 100 | $CH_3$ | $CH_3$ | —$OCH_2$— | 2,6-$Cl_2$—$C_6H_3$ | |
| 101 | $CH_3$ | $CH_3$ | —$OCH_2$— | 3,5-$Cl_2$—$C_6H_3$ | |
| 102 | $CH_3$ | $CH_3$ | —$OCH_2$— | 2,4,6-$Cl_3$—$C_6H_2$ | |
| 103 | $CH_3$ | $CH_3$ | —$OCH_2$— | 2-$CH_3$—$C_6H_4$ | |
| 104 | $CH_3$ | $CH_3$ | —$OCH_2$— | 3-$CH_3$—$C_6H_4$ | |
| 105 | $CH_3$ | $CH_3$ | —$OCH_2$— | 4-$CH_3$—$C_6H_4$ | |
| 106 | $CH_3$ | $CH_3$ | —$OCH_2$— | 4-t-$C_4H_9$—$C_6H_4$ | |
| 107 | $CH_3$ | $CH_3$ | —$OCH_2$— | 2,4-$(CH_3)_2$—$C_6H_3$ | |
| 108 | $CH_3$ | $CH_3$ | —$OCH_2$— | 2,6-$(CH_3)_2$—$C_6H_3$ | |
| 109 | $CH_3$ | $CH_3$ | —$OCH_2$— | 2,4,6-$(CH_3)_3$—$C_6H_2$ | |
| 110 | $CH_3$ | $CH_3$ | —$OCH_2$— | 2-$OCH_3$—$C_6H_4$ | |
| 111 | $CH_3$ | $CH_3$ | —$OCH_2$— | 3-$OCH_3$—$C_6H_4$ | |
| 112 | $CH_3$ | $CH_3$ | —$OCH_2$— | 4-$OCH_3$—$C_6H_4$ | |
| 113 | $CH_3$ | $CH_3$ | —$OCH_2$— | 2-$CF_3$—$C_6H_4$ | |
| 114 | $CH_3$ | $CH_3$ | —$OCH_2$— | 3-$CF_3$—$C_6H_4$ | |
| 115 | $CH_3$ | $CH_3$ | —$OCH_2$— | 4-$CF_3$—$C_6H_4$ | |
| 116 | $CH_3$ | $CH_3$ | —$OCH_2$— | 4-O-t-$C_4H_9$—$C_6H_4$ | |
| 117 | $CH_3$ | $CH_3$ | —$OCH_2$— | 4-O—$C_6H_5$—$C_6H_4$ | |
| 118 | $CH_3$ | $CH_3$ | —$OCH_2$— | 4-$C_6H_5$—$C_6H_4$ | |
| 119 | $CH_3$ | $CH_3$ | —$OCH_2$— | 2-Br—$C_6H_4$ | |
| 120 | $CH_3$ | $CH_3$ | —$OCH_2$— | 4-Br—$C_6H_4$ | |
| 121 | $CH_3$ | $CH_3$ | —$SCH_2$— | $C_6H_5$ | |
| 122 | $CH_3$ | $CH_3$ | —$SCH_2$— | 2-F—$C_6H_4$ | |
| 123 | $CH_3$ | $CH_3$ | —$SCH_2$— | 3-F—$C_6H_4$ | |
| 124 | $CH_3$ | $CH_3$ | —$SCH_2$— | 4-F—$C_6H_4$ | |
| 125 | $CH_3$ | $CH_3$ | —$SCH_2$— | 2-Cl—$C_6H_4$ | |
| 126 | $CH_3$ | $CH_3$ | —$SCH_2$— | 3-Cl—$C_6H_4$ | |

TABLE 1-continued

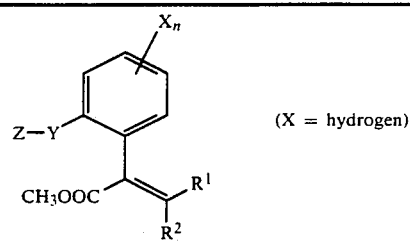

(X = hydrogen)

| No. | R¹ | R² | Y | Z | Data |
|---|---|---|---|---|---|
| 127 | $CH_3$ | $CH_3$ | $-SCH_2-$ | $4\text{-}Cl-C_6H_4$ | |
| 128 | $CH_3$ | $CH_3$ | $-SCH_2-$ | $2Cl,6F-C_6H_3$ | |
| 129 | $CH_3$ | $CH_3$ | $-SCH_2-$ | $2,4\text{-}Cl_2-C_6H_3$ | |
| 130 | $CH_3$ | $CH_3$ | $-SCH_2-$ | $2,6\text{-}Cl_2-C_6H_3$ | |
| 131 | $CH_3$ | $CH_3$ | $-SCH_2-$ | $3,5\text{-}Cl_2-C_6H_3$ | |
| 132 | $CH_3$ | $CH_3$ | $-SCH_2-$ | $2,4,6\text{-}Cl_3-C_6H_2$ | |
| 133 | $CH_3$ | $CH_3$ | $-SCH_2-$ | $2\text{-}CH_3-C_6H_4$ | |
| 134 | $CH_3$ | $CH_3$ | $-SCH_2-$ | $3\text{-}CH_3-C_6H_4$ | |
| 135 | $CH_3$ | $CH_3$ | $-SCH_2-$ | $4\text{-}CH_3-C_6H_4$ | |
| 136 | $CH_3$ | $CH_3$ | $-SCH_2-$ | $4\text{-}t\text{-}C_4H_9-C_6H_4$ | |
| 137 | $CH_3$ | $CH_3$ | $-SCH_2-$ | $2,4\text{-}(CH_3)_2-C_6H_3$ | |
| 138 | $CH_3$ | $CH_3$ | $-SCH_2-$ | $2,6\text{-}(CH_3)_2-C_6H_3$ | |
| 139 | $CH_3$ | $CH_3$ | $-SCH_2-$ | $2,4,6\text{-}(CH_3)_3-C_6H_2$ | |
| 140 | $CH_3$ | $CH_3$ | $-SCH_2-$ | $2\text{-}OCH_3-C_6H_4$ | |
| 141 | $CH_3$ | $CH_3$ | $-SCH_2-$ | $3\text{-}OCH_3-C_6H_4$ | |
| 142 | $CH_3$ | $CH_3$ | $-SCH_2-$ | $4\text{-}OCH_3-C_6H_4$ | |
| 143 | $CH_3$ | $CH_3$ | $-SCH_2-$ | $2\text{-}CF_3-C_6H_4$ | |
| 144 | $CH_3$ | $CH_3$ | $-SCH_2-$ | $3\text{-}CF_3-C_6H_4$ | |
| 145 | $CH_3$ | $CH_3$ | $-SCH_2-$ | $4\text{-}CF_3-C_6H_4$ | |
| 146 | $CH_3$ | $CH_3$ | $-SCH_2-$ | $4\text{-}O\text{-}t\text{-}C_4H_9-C_6H_4$ | |
| 147 | $CH_3$ | $CH_3$ | $-SCH_2-$ | $4\text{-}O-C_6H_5-C_6H_4$ | |
| 148 | $CH_3$ | $CH_3$ | $-SCH_2-$ | $4\text{-}C_6H_5-C_6H_4$ | |
| 149 | $CH_3$ | $CH_3$ | $-SCH_2-$ | $2\text{-}Br-C_6H_4$ | |
| 150 | $CH_3$ | $CH_3$ | $-SCH_2-$ | $4\text{-}Br-C_6H_4$ | |
| 151 | $CH_3$ | $CH_3$ | $-CO-OCH_2-$ | $C_6H_5$ | mp.: 75° C.; IR(KBr): 1713, 1630, 1276, 1215, 1112, 1092, 758, 708 $cm^{-1}$ |
| 152 | $CH_3$ | $CH_3$ | $-CO-OCH_2-$ | $2\text{-}F-C_6H_4$ | |
| 153 | $CH_3$ | $CH_3$ | $-CO-OCH_2-$ | $3\text{-}F-C_6H_4$ | |
| 154 | $CH_3$ | $CH_3$ | $-CO-OCH_2-$ | $4\text{-}F-C_6H_4$ | |
| 155 | $CH_3$ | $CH_3$ | $-CO-OCH_2-$ | $2\text{-}Cl-C_6H_4$ | |
| 156 | $CH_3$ | $CH_3$ | $-CO-OCH_2-$ | $3\text{-}Cl-C_6H_4$ | |
| 157 | $CH_3$ | $CH_3$ | $-CO-OCH_2-$ | $4\text{-}Cl-C_6H_4$ | |
| 158 | $CH_3$ | $CH_3$ | $-CO-OCH_2-$ | $2Cl,6F-C_6H_3$ | |
| 159 | $CH_3$ | $CH_3$ | $-CO-OCH_2-$ | $2,4\text{-}Cl_2-C_6H_3$ | |
| 160 | $CH_3$ | $CH_3$ | $-CO-OCH_2-$ | $2,6\text{-}Cl_2-C_6H_3$ | |
| 161 | $CH_3$ | $CH_3$ | $-CO-OCH_2-$ | $3,5\text{-}Cl_2-C_6H_3$ | |
| 162 | $CH_3$ | $CH_3$ | $-CO-OCH_2-$ | $2,4,6\text{-}Cl_3-C_6H_2$ | |
| 163 | $CH_3$ | $CH_3$ | $-CO-OCH_2-$ | $2\text{-}CH_3-C_6H_4$ | |
| 164 | $CH_3$ | $CH_3$ | $-CO-OCH_2-$ | $3\text{-}CH_3-C_6H_4$ | |
| 165 | $CH_3$ | $CH_3$ | $-CO-OCH_2-$ | $4\text{-}CH_3-C_6H_4$ | |
| 166 | $CH_3$ | $CH_3$ | $-CO-OCH_2-$ | $4\text{-}t\text{-}C_4H_9-C_6H_4$ | |
| 167 | $CH_3$ | $CH_3$ | $-CO-OCH_2-$ | $2,4\text{-}(CH_3)_2-C_6H_3$ | |
| 168 | $CH_3$ | $CH_3$ | $-CO-OCH_2-$ | $2,6\text{-}(CH_3)_2-C_6H_3$ | |
| 169 | $CH_3$ | $CH_3$ | $-CO-OCH_2-$ | $2,4,6\text{-}(CH_3)_3-C_6H_2$ | |
| 170 | $CH_3$ | $CH_3$ | $-CO-OCH_2-$ | $2\text{-}OCH_3-C_6H_4$ | |
| 171 | $CH_3$ | $CH_3$ | $-CO-OCH_2-$ | $3\text{-}OCH_3-C_6H_4$ | |
| 172 | $CH_3$ | $CH_3$ | $-CO-OCH_2-$ | $4\text{-}OCH_3-C_6H_4$ | |
| 173 | $CH_3$ | $CH_3$ | $-CO-OCH_2-$ | $2\text{-}CF_3-C_6H_4$ | |
| 174 | $CH_3$ | $CH_3$ | $-CO-OCH_2-$ | $3\text{-}CF_3-C_6H_4$ | |
| 175 | $CH_3$ | $CH_3$ | $-CO-OCH_2-$ | $4\text{-}CF_3-C_6H_4$ | |
| 176 | $CH_3$ | $CH_3$ | $-CO-OCH_2-$ | $4\text{-}O\text{-}t\text{-}C_4H_9-C_6H_4$ | |
| 177 | $CH_3$ | $CH_3$ | $-CO-OCH_2-$ | $4\text{-}O-C_6H_5-C_6H_4$ | |
| 178 | $CH_3$ | $CH_3$ | $-CO-OCH_2-$ | $4\text{-}C_6H_5-C_6H_4$ | |
| 179 | $CH_3$ | $CH_3$ | $-CO-OCH_2-$ | $2\text{-}Br-C_6H_4$ | |
| 180 | $CH_3$ | $CH_3$ | $-CO-OCH_2-$ | $4\text{-}Br-C_6H_4$ | |
| 181 | $CH_3$ | $CH_3$ | $-C\equiv C-$ | $C_6H_5$ | |
| 182 | $CH_3$ | $CH_3$ | $-C\equiv C-$ | $2\text{-}Cl-C_6H_4$ | |
| 183 | $CH_3$ | $CH_3$ | $-C\equiv C-$ | $3\text{-}Cl-C_6H_4$ | |
| 184 | $CH_3$ | $CH_3$ | $-C\equiv C-$ | $4\text{-}Cl-C_6H_4$ | |
| 185 | $CH_3$ | $CH_3$ | $-O-$ | $C_6H_5$ | |
| 186 | $CH_3$ | $CH_3$ | $-O-$ | $2\text{-}Cl-C_6H_4$ | |
| 187 | $CH_3$ | $CH_3$ | $-O-$ | $3\text{-}Cl-C_6H_4$ | |
| 188 | $CH_3$ | $CH_3$ | $-O-$ | $4\text{-}Cl-C_6H_4$ | |
| 189 | $CH_3$ | $CH_3$ | $-O-$ | $2\text{-}CH_3-C_6H_4$ | |
| 190 | $CH_3$ | $CH_3$ | $-O-$ | $4\text{-}CH_3-C_6H_4$ | |
| 191 | $CH_3$ | $CH_3$ | $-O-$ | $4\text{-}C_6H_5-C_6H_4$ | |
| 192 | $CH_3$ | $CH_3$ | $-O-$ | $1\text{-}C_{10}H_7$ | |
| 193 | $CH_3$ | $CH_3$ | $-O-$ | $CH_3$ | |

TABLE 1-continued

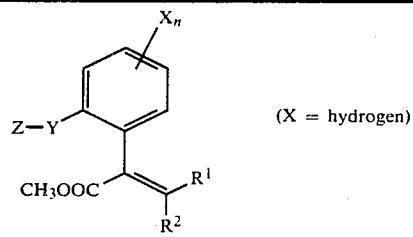

(X = hydrogen)

| No. | R$^1$ | R$^2$ | Y | Z | Data |
|---|---|---|---|---|---|
| 194 | CH$_3$ | CH$_3$ | —O— | CH$_2$CH=CH$_2$ | |
| 195 | CH$_3$ | CH$_3$ | —O— | CH$_2$CH=C(CH$_3$)$_2$ | |
| 196 | CH$_3$ | CH$_3$ | —O— | geranyl | |
| 197 | CH$_3$ | CH$_3$ | —O— | tetrahydrogeranyl | |
| 198 | CH$_3$ | CH$_3$ | —O— | 2-OCH$_3$—C$_6$H$_4$ | |
| 199 | CH$_3$ | CH$_3$ | —O— | 2,3-(OCH$_3$)$_2$—C$_6$H$_3$ | |
| 200 | CH$_3$ | CH$_3$ | —S— | C$_6$H$_5$ | |
| 201 | CH$_3$ | CH$_3$ | —S— | 2-Cl—C$_6$H$_4$ | |
| 202 | CH$_3$ | CH$_3$ | —S— | 3-Cl—C$_6$H$_4$ | |
| 203 | CH$_3$ | CH$_3$ | —S— | 4-Cl—C$_6$H$_4$ | |
| 204 | CH$_3$ | CH$_3$ | —S— | 2-CH$_3$—C$_6$H$_4$ | |
| 205 | CH$_3$ | CH$_3$ | —S— | 4-CH$_3$—C$_6$H$_4$ | |
| 206 | CH$_3$ | CH$_3$ | —S— | 4-C$_6$H$_5$—C$_6$H$_4$ | |
| 207 | CH$_3$ | CH$_3$ | —S— | CH$_3$ | |
| 208 | CH$_3$ | CH$_3$ | —S— | geranyl | |
| 209 | CH$_3$ | CH$_3$ | —S— | 2-pyridyl | |
| 210 | CH$_3$ | CH$_3$ | —S— | 2-pyrimidyl | |
| 211 | CH$_3$ | CH$_3$ | —COO— | C$_6$H$_5$ | |
| 212 | CH$_3$ | CH$_3$ | —COO— | 2-Cl—C$_6$H$_4$ | |
| 213 | CH$_3$ | CH$_3$ | —COO— | 3-Cl—C$_6$H$_4$ | |
| 214 | CH$_3$ | CH$_3$ | —COO— | 4-Cl—C$_6$H$_4$ | |
| 215 | CH$_3$ | CH$_3$ | —COO— | 2-CH$_3$—C$_6$H$_4$ | |
| 216 | CH$_3$ | CH$_3$ | —COO— | 4-CH$_3$—C$_6$H$_4$ | |
| 217 | CH$_3$ | CH$_3$ | —COO— | 4-C$_6$H$_5$—C$_6$H$_4$ | |
| 218 | CH$_3$ | CH$_3$ | —O—CO— | C$_6$H$_5$ | |
| 219 | CH$_3$ | CH$_3$ | —O—CO— | 2-Cl—C$_6$H$_4$ | |
| 220 | CH$_3$ | CH$_3$ | —O—CO— | 3-Cl—C$_6$H$_4$ | |
| 221 | CH$_3$ | CH$_3$ | —O—CO— | 4-Cl—C$_6$H$_4$ | |
| 222 | CH$_3$ | CH$_3$ | —O—CO— | 2-CH$_3$—C$_6$H$_4$ | |
| 223 | CH$_3$ | CH$_3$ | —O—CO— | CH$_3$ | |
| 224 | CH$_3$ | CH$_3$ | —O—CO— | t-C$_4$H$_9$ | |
| 225 | CH$_3$ | CH$_3$ | —O—CO— | CH$_2$C$_6$H$_5$ | |
| 226 | CH$_3$ | CH$_3$ | —HNCO—O | C$_6$H$_5$ | |
| 227 | CH$_3$ | CH$_3$ | —HNCO—O | 2-Cl—C$_6$H$_4$ | |
| 228 | CH$_3$ | CH$_3$ | —HNCO—O | 4-Cl—C$_6$H$_4$ | |
| 229 | CH$_3$ | CH$_3$ | —HNCO—O | C$_6$H$_{11}$ | |
| 230 | CH$_3$ | CH$_3$ | —HNCO—O | n-C$_4$H$_9$ | |
| 231 | CH$_3$ | CH$_3$ | —CH=CH— | CH$_2$C(CH$_3$)$_3$ | |
| 232 | CH$_3$ | CH$_3$ | —CH=CH— | CH=C(CH$_3$)CH$_2$CH$_2$CH=C(CH$_3$)$_2$ | |
| 233 | CH$_3$ | CH$_3$ | —CH=CH— | CH$_2$CH(CH$_3$)CH$_2$CH$_2$CH=C(CH$_3$)$_2$ | |
| 234 | CH$_3$ | CH$_3$ | —CH=CH— | CH=C(C$_2$H$_5$)CH$_2$CH$_2$CH$_2$CH$_3$ | |
| 235 | CH$_3$ | CH$_3$ | —CH=CH— | CH$_2$CH(C$_2$H$_5$)CH$_2$CH$_2$CH$_2$CH$_3$ | |
| 236 | CH$_3$ | CH$_3$ | —CH=CH— | CH$_2$CH(CH$_3$)CH$_2$CH$_2$CH$_2$CH(CH$_3$)$_2$ | |
| 237 | CH$_3$ | CH$_3$ | —CH=CH— | cyclopropyl | |
| 238 | CH$_3$ | CH$_3$ | —CH=CH— | 1-methycyclopropyl | |
| 239 | CH$_3$ | CH$_3$ | —CH=CH— | CH=CH—C$_6$H$_5$ | |
| 240 | CH$_3$ | CH$_3$ | —CH=CH— | CH$_2$—CH$_2$—C$_6$H$_5$ | |
| 241 | CH$_3$ | CH$_3$ | —CH=CH— | C(CH$_3$)$_3$ | |
| 242 | CH$_3$ | CH$_3$ | —CH=CH— | cyclohexyl | |
| 243 | CH$_3$ | CH$_3$ | —CH=CH— | (CH$_2$CH(CH$_3$)CH$_2$CH$_2$)$_2$CH$_2$CH(CH$_3$)$_2$ | |
| 244 | CH$_3$ | CH$_3$ | —CH=CH— | 2-furyl | |
| 245 | CH$_3$ | CH$_3$ | —CH=CH— | 2-thiophenyl | |
| 246 | CH$_3$ | CH$_3$ | —CH=CH— | CF$_3$ | |
| 247 | CH$_3$ | CH$_3$ | —CH=CH— | CCl$_3$ | |
| 248 | CH$_3$ | CH$_3$ | —CH$_2$CH$_2$— | C(CH$_3$)$_3$ | |
| 249 | CH$_3$ | CH$_3$ | —CH$_2$CH$_2$— | CH$_2$C(CH$_3$)$_3$ | |
| 250 | CH$_3$ | CH$_3$ | —CH$_2$CH$_2$— | CH$_2$CH(CH$_3$)CH$_2$CH$_2$CH$_2$CH(CH$_3$)$_2$ | |
| 251 | CH$_3$ | CH$_3$ | —CH$_2$CH$_2$— | CH$_2$CH(C$_2$H$_5$)CH$_2$CH$_2$CH$_2$CH$_3$ | |
| 252 | CH$_3$ | CH$_3$ | —CH$_2$CH$_2$— | (CH$_2$CH(CH$_3$)CH$_2$CH$_2$)$_2$CH$_2$CH(CH$_3$)$_2$ | |
| 253 | CH$_3$ | CH$_3$ | —CH$_2$CH$_2$— | cyclopropyl | |
| 254 | CH$_3$ | CH$_3$ | —CH$_2$CH$_2$— | 1-methyl-cyclopropyl | |
| 255 | CH$_3$ | CH$_3$ | —CH$_2$CH$_2$— | cyclohexyl | |
| 256 | CH$_3$ | CH$_3$ | —CH$_2$CH$_2$— | CH$_2$CH$_2$C$_6$H$_5$ | |
| 257 | CH$_3$ | CH$_3$ | —CH$_2$CH$_2$— | CH$_2$CH$_2$CH$_2$C$_6$H$_5$ | |
| 258 | CH$_3$ | CH$_3$ | —CH$_2$CH$_2$— | CF$_3$ | |
| 259 | CH$_3$ | CH$_3$ | —CH$_2$CH$_2$— | CCl$_3$ | |
| 260 | CH$_3$ | CH$_3$ | —CH$_2$CH$_2$— | O—C$_6$H$_5$ | |
| 261 | CH$_3$ | CH$_3$ | —CH$_2$O— | CH$_2$CH(CH$_3$)CH$_2$CH$_2$CH=C(CH$_3$)$_2$ | |
| 262 | CH$_3$ | CH$_3$ | —CH$_2$O— | (CH=C(CH$_3$)CH$_2$CH$_2$)$_2$CH=C(CH$_3$)$_2$ | |

TABLE 1-continued $$\text{structure with } Z-Y, X_n \text{ on benzene ring, } CH_3OOC-C=C(R^1)(R^2)$$

(X = hydrogen)

| No. | R¹ | R² | Y | Z | Data |
|---|---|---|---|---|---|
| 263 | CH₃ | CH₃ | —CH₂O— | (CH₂CH(CH₃)CH₂CH₂)₂CH₂CH(CH₃)₂ | |
| 264 | CH₃ | CH₃ | —CH₂O— | CH=CHC₆H₅ | |
| 265 | CH₃ | CH₃ | —CH₂O— | CH₂—CH₂C₆H₅ | |
| 266 | CH₃ | CH₃ | —CH₂O— | CH₂—O—C₆H₅ | |
| 267 | CH₃ | CH₃ | —OCH₂— | CH₃ | |
| 268 | CH₃ | CH₃ | —OCH₂— | C₂H₅ | |
| 269 | CH₃ | CH₃ | —OCH₂— | n-C₃H₇ | |
| 270 | CH₃ | CH₃ | —OCH₂— | i-C₃H₇ | |
| 271 | CH₃ | CH₃ | —OCH₂— | CH₂CH=CH₂ | |
| 272 | CH₃ | CH₃ | —OCH₂— | CH₂CH=C(CH₃)₂ | |
| 273 | CH₃ | CH₃ | —OCH₂— | CH₂C₆H₅ | |
| 274 | CH₃ | CH₃ | —OCH₂— | CH₂—(2-Cl—C₆H₄) | |
| 275 | CH₃ | CH₃ | —OCH₂— | CH₂(2-CH₃—C₆H₄) | |
| 276 | CH₃ | CH₃ | —OCH₂— | CH₂CH₂C₆H₅ | |
| 277 | CH₃ | CH₃ | —OCH₂— | CH₂CH₂OC₆H₅ | |
| 278 | CH₃ | CH₃ | —OCH₂— | (CH₂)₄OC₆H₅ | |
| 279 | CH₃ | CH₃ | —CO—OCH₂— | cyclopropyl | |
| 280 | CH₃ | CH₃ | —CO—OCH₂— | 1-methylcyclopropyl | oil; IR(film): 1720, 1322, 1222, 1156, 1090, 755 cm⁻¹ |
| 281 | CH₃ | CH₃ | —CO—OCH₂— | 2-methylcyclopropyl | |
| 282 | CH₃ | CH₃ | —CO—OCH₂— | 2,2-dichlorocyclopropyl | |
| 283 | CH₃ | CH₃ | —CO—OCH₂— | A1* | |
| 284 | CH₃ | CH₃ | —CO—OCH₂— | A2* | |
| 285 | CH₃ | CH₃ | —CO—OCH₂— | A3* | |
| 286 | CH₃ | CH₃ | —CO—OCH₂— | A4* | |
| 287 | CH₃ | CH₃ | —CO—OCH₂— | A5* | |
| 288 | CH₃ | CH₃ | —CO—OCH₂— | A6* | |
| 289 | CH₃ | CH₃ | —CO—OCH₂— | A7* | |
| 290 | CH₃ | CH₃ | —CO—OCH₂— | A8* | |
| 291 | CH₃ | CH₃ | —CO—OCH₂— | A9* | |
| 292 | CH₃ | CH₃ | —CO—OCH₂— | A10* | |
| 293 | CH₃ | CH₃ | —CO—OCH₂— | A11* | |
| 294 | CH₃ | CH₃ | —CO—OCH₂— | CH₃ | |
| 295 | CH₃ | CH₃ | —CO—OCH₂— | C₂H₅ | |
| 296 | CH₃ | CH₃ | —CO—OCH₂— | n-C₃H₇ | |
| 297 | CH₃ | CH₃ | —CO—OCH₂— | i-C₃H₇ | |
| 298 | CH₃ | CH₃ | —CO—OCH₂— | CH(CH₃)CH₂CH₃ | |
| 299 | CH₃ | CH₃ | —CO—OCH₂— | tert-C₄H₉ | oil; IR(film): 1727, 1718, 1282, 1222, 1150, 1090, 754 cm⁻¹ |
| 300 | CH₃ | CH₃ | —CO—OCH₂— | CH(CH₃)CH₂CH₂CH₂CH₃ | |
| 301 | CH₃ | CH₃ | —CO—OCH₂— | CH(C₂H₅)CH₂CH₂CH₂CH₃ | |
| 302 | CH₃ | CH₃ | —CO—OCH₂— | CH(iso-C₃H₇)CH₂CH₂CH(CH₃)₂ | |
| 303 | CH₃ | CH₃ | —CO—OCH₂— | CH=CH—C₆H₅ | |
| 304 | CH₃ | CH₃ | —CO—OCH₂— | CH=CH-(2-chloro)-C₆H₄ | |
| 305 | CH₃ | CH₃ | —CO—OCH₂— | CH=CH-(4-tert.butyl)-C₆H₄ | |
| 306 | CH₃ | CH₃ | —CO—OCH₂— | CH₂CH₂—C₆H₅ | |
| 307 | CH₃ | CH₃ | —CO—OCH₂— | (CH₂)₄C₆H₅ | |
| 308 | CH₃ | CH₃ | —CO—OCH₂— | CH₂CH₂—OC₆H₅ | |
| 309 | CH₃ | CH₃ | —CO—OCH₂— | (CH₂)₄—OC₆H₅ | |
| 310 | CH₃ | CH₃ | —CO—OCH₂— | CH(Cl)C₆H₅ | |

*for formulae see previous text

TABLE 2

(Structure: phenyl ring with $X_n$, $Z-Y-$ substituent, and $CH_3OOC-C(=CR^1R^2)-$ group)

(X = hydrogen)

| No. | R¹ | R² | Y | Z |
|---|---|---|---|---|
| 1a | Cl | Cl | —CH=CH— | C₆H₅ |
| 2a | Cl | Cl | —CH₂CH₂— | C₆H₅ |
| 3a | Cl | Cl | —OCH₂— | C₆H₅ |
| 4a | Cl | Cl | —CH₂—O— | C₆H₅ |
| 5a | Cl | Cl | —SCH₂— | C₆H₅ |
| 6a | Cl | Cl | —O— | C₆H₅ |
| 7a | Br | Br | —CH=CH— | C₆H₅ |
| 8a | Br | Br | —CH₂CH₂— | C₆H₅ |
| 9a | Br | Br | —OCH₂— | C₆H₅ |
| 10a | Br | Br | —CH₂O— | C₆H₅ |
| 11a | Br | Br | —SCH₂— | C₆H₅ |
| 12a | Br | Br | —O— | C₆H₅ |
| 13a | C₂H₅ | C₂H₅ | —CH=CH— | C₆H₅ |
| 14a | C₂H₅ | C₂H₅ | —CH₂CH₂— | C₆H₅ |
| 15a | C₂H₅ | C₂H₅ | —OCH₂— | C₆H₅ |
| 16a | C₂H₅ | C₂H₅ | —CH₂O— | C₆H₅ |
| 17a | C₂H₅ | C₂H₅ | —SCH₂— | C₆H₅ |
| 18a | C₂H₅ | C₂H₅ | —O— | C₆H₅ |
| 19a | C₂H₅ | C₂H₅ | —OCH₂— | 2-Cl—C₆H₄ |
| 20a | C₂H₅ | C₂H₅ | —CH₂O— | 2-Cl—C₆H₄ |
| 21a | C₂H₅ | C₂H₅ | —CO—OCH₂ | C₆H₅ |
| 22a | C₂H₅ | C₂H₅ | —CO—OCH₂— | 1-methylcyclopropyl |
| 23a | C₂H₅ | C₂H₅ | —CO—OCH₂— | t-C₄H₉ |
| 24a | C₂H₅ | C₂H₅ | —CO—OCH₂— | 2,2-dichlorocyclopropyl |
| 25a | C₂H₅ | C₂H₅ | —CO—OCH₂— | CH(C₂H₅)CH₂CH₂CH₂CH₃ |
| 26a | C₂H₅ | C₂H₅ | —CO—OCH₂— | CH=CH—C₆H₅ |
| 27a | C₂H₅ | C₂H₅ | —CO—OCH₂ | A1* |
| 28a | C₂H₅ | C₂H₅ | —CO—OCH₂— | A6* |
| 29a | n-C₃H₇ | n-C₃H₇ | —CH=CH— | C₆H₅ |
| 30a | n-C₃H₇ | n-C₃H₇ | —CH₂CH₂— | C₆H₅ |
| 31a | n-C₃H₇ | n-C₃H₇ | —CH₂O— | C₆H₅ |
| 32a | n-C₃H₇ | n-C₃H₇ | —OCH₂— | C₆H₅ |
| 33a | n-C₃H₇ | n-C₃H₇ | —CO—OCH₂— | C₆H₅ |
| 34a | OCH₃ | OCH₃ | —CH=CH— | C₆H₅ |
| 35a | OCH₃ | OCH₃ | —CH=CH— | 3-Cl—C₆H₄ |
| 36a | OCH₃ | OCH₃ | —CH=CH— | 3-CF₃—C₆H₄ |
| 37a | OCH₃ | OCH₃ | —CH=CH— | 2-CH₃—C₆H₄ |
| 38a | OCH₃ | OCH₃ | —CH=CH— | 3-CH₃—C₆H₄ |
| 39a | OCH₃ | OCH₃ | —CH₂CH₂— | C₆H₅ |
| 40a | OCH₃ | OCH₃ | —CH₂CH₂— | 3-Cl—C₆H₄ |
| 41a | OCH₃ | OCH₃ | —CH₂CH₂— | 3-CF₃—C₆H₄ |
| 42a | OCH₃ | OCH₃ | —CH₂CH₂— | 3-CH₃—C₆H₄ |
| 43a | OCH₃ | OCH₃ | —CH₂CH₂— | 2-Cl—C₆H₄ |
| 44a | OCH₃ | OCH₃ | —CH₂O— | C₆H₅ |
| 45a | OCH₃ | OCH₃ | —CH₂O— | 3-Cl—C₆H₄ |
| 46a | OCH₃ | OCH₃ | —CH₂O— | 2,4-Cl₂—C₆H₃ |
| 47a | OCH₃ | OCH₃ | —CH₂O— | 2-Br—C₆H₄ |
| 48a | OCH₃ | OCH₃ | —OCH₂— | C₆H₅ |
| 49a | OCH₃ | OCH₃ | —OCH₂— | 3-Cl—C₆H₄ |
| 50a | OCH₃ | OCH₃ | —OCH₂ | 2,4-Cl₂—C₆H₃ |
| 51a | OCH₃ | OCH₃ | —OCH₂— | 2-Br—C₆H₄ |
| 52a | OCH₃ | OCH₃ | —S—CH₂— | C₆H₅ |
| 53a | OCH₃ | OCH₃ | —CO—OCH₂— | C₆H₅ |
| 54a | OCH₃ | OCH₃ | —CO—OCH₂— | tert.-C₄H₉ |
| 55a | OCH₃ | OCH₃ | —CO—OCH₂— | 1-methylcyclopropyl |
| 56a | OCH₃ | OCH₃ | —CO—OCH₂— | 2,2-dichlorocyclopropyl |
| 57a | OCH₃ | OCH₃ | —CO—OCH₂— | CH(C₂H₅)CH₂CH₂CH₂CH₃ |
| 58a | OCH₃ | OCH₃ | —CO—OCH₂— | CH=CH—C₆H₅ |
| 59a | OCH₃ | OCH₃ | —CO—OCH₂— | C₆H₅ |
| 60a | OCH₃ | OCH₃ | —CO—OCH₂— | A1* |
| 61a | OCH₃ | OCH₃ | —CO—OCH₂— | A6* |
| 62a | OC₂H₅ | OC₂H₅ | —CH=CH— | C₆H₅ |
| 63a | OC₂H₅ | OC₂H₅ | —CH₂—CH₂— | C₆H₅ |
| 64a | OC₂H₅ | OC₂H₅ | —CH₂O— | C₆H₅ |
| 65a | OC₂H₅ | OC₂H₅ | —OCH₂— | C₆H₅ |
| 66a | OC₂H₅ | OC₂H₅ | —SCH₂— | C₆H₅ |
| 67a | OC₂H₅ | OC₂H₅ | —O— | C₆H₅ |
| 68a | OC₂H₅ | OC₂H₅ | —CO—OCH₂— | C₆H₅ |
| 69a | OC₂H₅ | OC₂H₅ | —CO—OCH₂— | 1-methylcyclopropyl |

TABLE 2-continued

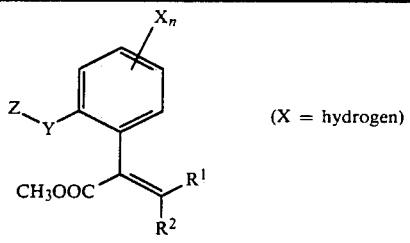

(X = hydrogen)

| No. | $R^1$ | $R^2$ | Y | Z | Data |
|---|---|---|---|---|---|
| 70a | $OC_2H_5$ | $OC_2H_5$ | $-CO-OCH_2-$ | A1* | |
| 71a | $OC_2H_5$ | $OC_2H_5$ | $-CO-OCH_2-$ | A6* | |
| 72a | $CH_2OCH_3$ | $CH_2OCH_3$ | $-CH=CH-$ | $C_6H_5$ | |
| 73a | $CH_2OCH_3$ | $CH_2OCH_3$ | $-CH_2-CH_2-$ | $C_6H_5$ | |
| 74a | $CH_2OCH_3$ | $CH_2OCH_3$ | $-CH_2O-$ | $C_6H_5$ | |
| 75a | $CH_2OCH_3$ | $CH_2OCH_3$ | $-OCH_2-$ | $C_6H_5$ | |
| 76a | $CH_2OCH_3$ | $CH_2OCH_3$ | $-SCH_2-$ | $C_6H_5$ | |
| 77a | $CH_2OCH_3$ | $CH_2OCH_3$ | $-O-$ | $C_6H_5$ | |
| 78a | $CH_2OCH_3$ | $CH_2OCH_3$ | $-CO-OCH_2-$ | $C_6H_5$ | |
| 79a | $CH_2OCH_3$ | $CH_2OCH_3$ | $-CO-OCH_2-$ | 1-methylcyclopropyl | |
| 80a | $SCH_3$ | $SCH_3$ | $-CH=CH-$ | $C_6H_5$ | |
| 81a | $SCH_3$ | $SCH_3$ | $-CH=CH-$ | $2-CH_3-C_6H_4$ | |
| 82a | $SCH_3$ | $SCH_3$ | $-CH_2CH_2-$ | $C_6H_5$ | |
| 83a | $SCH_3$ | $SCH_3$ | $-CH_2CH_2-$ | $3-Cl-C_6H_4$ | |
| 84a | $SCH_3$ | $SCH_3$ | $-CH_2CH_2-$ | $3-CH_3-C_6H_4$ | |
| 85a | $SCH_3$ | $SCH_3$ | $-CH_2CH_2-$ | $3-CF_3-C_6H_4$ | |
| 86a | $SCH_3$ | $SCH_3$ | $-CH_2O-$ | $C_6H_5$ | |
| 87a | $SCH_3$ | $SCH_3$ | $-CH_2O-$ | $3-Cl-C_6H_4$ | |
| 88a | $SCH_3$ | $SCH_3$ | $-OCH_2-$ | $C_6H_5$ | |
| 89a | $SCH_3$ | $SCH_3$ | $-S-CH_2-$ | $C_6H_5$ | |
| 90a | $SCH_3$ | $SCH_3$ | $-CO-OCH_2-$ | $C_6H_5$ | |
| 91a | $SCH_3$ | $SCH_3$ | $-CO-OCH_2-$ | 1-methylcyclopropyl | |
| 92a | $SCH_3$ | $SCH_3$ | $-CO-OCH_2-$ | A1* | |
| 93a | $SCH_3$ | $SCH_3$ | $-CO-OCH_2-$ | A6* | |
| 94a | $SC_2H_5$ | $SC_2H_5$ | $-CH=CH-$ | $C_6H_5$ | |
| 95a | $SC_2H_5$ | $SC_2H_5$ | $-CH_2CH_2-$ | $C_6H_5$ | |
| 96a | $SC_2H_5$ | $SC_2H_5$ | $-CH_2O-$ | $C_6H_5$ | |
| 97a | $SC_2H_5$ | $SC_2H_5$ | $-OCH_2-$ | $C_6H_5$ | |
| 98a | $SC_2H_5$ | $SC_2H_5$ | $-SCH_2-$ | $C_6H_5$ | |
| 99a | $SC_2H_5$ | $SC_2H_5$ | $-O-$ | $C_6H_5$ | |
| 100a | $SC_2H_5$ | $SC_2H_5$ | $-CO-OCH_2-$ | $C_6H_5$ | |
| 101a | $SC_2H_5$ | $SC_2H_5$ | $-CO-OCH_2$ | 1-methylcyclopropyl | |
| 102a | $CF_3$ | $CF_3$ | $-CH=CH-$ | $C_6H_5$ | |
| 103a | $CF_3$ | $CF_3$ | $-CH_2CH_2-$ | $C_6H_5$ | |
| 104a | $CF_3$ | $CF_3$ | $-CH_2O-$ | $C_6H_5$ | |
| 105a | $CF_3$ | $CF_3$ | $-OCH_2-$ | $C_6H_5$ | |
| 106a | $CF_3$ | $CF_3$ | $-SCH_2-$ | $C_6H_5$ | |
| 107a | $CF_3$ | $CF_3$ | $-O-$ | $C_6H_5$ | |
| 108a | $CF_3$ | $CF_3$ | $-CO-OCH_2-$ | $C_6H_5$ | |
| 109a | $CF_3$ | $CF_3$ | $-CO-OCH_2-$ | 1-methylcylopropyl | |
| 110a | $CH_3$ | $C_2H_5$ | $-CH=CH-$ | $C_6H_5$ | |
| 111a | $C_2H_5$ | $CH_3$ | $-CH=CH-$ | $C_6H_5$ | |
| 112a | $CH_3$ | $C_2H_5$ | $-CH_2CH_2-$ | $C_6H_5$ | |
| 113a | $C_2H_5$ | $CH_3$ | $-CH_2CH_2-$ | $C_6H_5$ | |
| 114a | $CH_3$ | $C_2H_5$ | $-CH_2O-$ | $C_6H_5$ | |
| 115a | $C_2H_5$ | $CH_3$ | $-CH_2O-$ | $C_6H_5$ | |
| 116a | $CH_3$ | $C_2H_5$ | $-OCH_2-$ | $C_6H_5$ | |
| 117a | $C_2H_5$ | $CH_3$ | $-OCH_2-$ | $C_6H_5$ | |
| 118a | $CH_3$ | $C_2H_5$ | $-CO-OCH_2-$ | $C_6H_5$ | |
| 119a | $C_2H_5$ | $CH_3$ | $-CO-OCH_2-$ | $C_6H_5$ | |
| 120a | $CH_3$ | $C_2H_5$ | $-CO-OCH_2-$ | 1-methylcyclopropyl | |
| 121a | $C_2H_5$ | $CH_3$ | $-CO-OCH_2-$ | 1-methylcyclopropyl | |
| 122a | $CH_3$ | $n-C_3H_7$ | $-CH=CH-$ | $C_6H_5$ | |
| 123a | $n-C_3H_7$ | $CH_3$ | $-CH=CH-$ | $C_6H_5$ | |
| 124a | $CH_3$ | $n-C_3H_7$ | $-CH_2CH_2-$ | $C_6H_5$ | |
| 125a | $n-C_3H_7$ | $CH_3$ | $-CH_2CH_2-$ | $C_6H_5$ | |
| 126a | $CH_3$ | $n-C_3H_7$ | $-CH_2O-$ | $C_6H_5$ | |
| 127a | $n-C_3H_7$ | $CH_3$ | $-CH_2O-$ | $C_6H_5$ | |
| 138a | $CH_3$ | $n-C_3H_7$ | $-OCH_2-$ | $C_6H_5$ | |
| 129a | $n-C_3H_7$ | $CH_3$ | $-OCH_2-$ | $C_6H_5$ | |
| 130a | $CH_3$ | $n-C_3H_7$ | $-CO-OCH_2-$ | $C_6H_5$ | |
| 131a | $n-C_3H_7$ | $CH_3$ | $-CO-OCH_2-$ | $C_6H_5$ | |
| 132a | $CH_3$ | $n-C_3H_7$ | $-CO-OCH_2-$ | 1-methylcyclopropyl | |
| 133a | $n-C_3H_7$ | $CH_3$ | $-CO-OCH_2-$ | 1-methylcyclopropyl | |
| 134a | $CH_3$ | $i-C_3H_7$ | $-CH=CH-$ | $C_6H_5$ | |
| 135a | $i-C_3H_7$ | $CH_3$ | $-CH=CH-$ | $C_6H_5$ | |
| 136a | $CH_3$ | $i-C_3H_7$ | $-CH_2CH_2-$ | $C_6H_5$ | |
| 137a | $i-C_3H_7$ | $CH_3$ | $-CH_2CH_2-$ | $C_6H_5$ | |
| 138a | $CH_3$ | $i-C_3H_7$ | $-CH_2O-$ | $C_6H_5$ | |

TABLE 2-continued (structure: phenyl ring with $X_n$ substituents, Z-Y group, and CH$_3$OOC-C=C(R$^1$)(R$^2$) sidechain) (X = hydrogen)

| No. | R$^1$ | R$^2$ | Y | Z | Data |
|---|---|---|---|---|---|
| 139a | i-C$_3$H$_7$ | CH$_3$ | —CH$_2$O— | C$_6$H$_5$ | |
| 140a | CH$_3$ | i-C$_3$H$_7$ | —OCH$_2$— | C$_6$H$_5$ | |
| 141a | i-C$_3$H$_7$ | CH$_3$ | —OCH$_2$— | C$_6$H$_5$ | |
| 142a | CH$_3$ | i-C$_3$H$_7$ | —CO—OCH$_2$— | C$_6$H$_5$ | |
| 143a | i-C$_3$H$_7$ | CH$_3$ | —CO—OCH$_2$— | C$_6$H$_5$ | |
| 144a | CH$_3$ | i-C$_3$H$_7$ | —CO—OCH$_2$— | 1-methylcyclopropyl | |
| 145a | i-C$_3$H$_7$ | CH$_3$ | —CO—OCH$_2$— | 1-methylcyclopropyl | |
| 146a | CH$_3$ | OCH$_3$ | —CH=CH— | C$_6$H$_5$ | |
| 147a | OCH$_3$ | CH$_3$ | —CH=CH— | C$_6$H$_5$ | |
| 148a | CH$_3$ | OCH$_3$ | —CH$_2$CH$_2$— | C$_6$H$_5$ | |
| 149a | OCH$_3$ | CH$_3$ | —CH$_2$CH$_2$— | C$_6$H$_5$ | |
| 150a | CH$_3$ | OCH$_3$ | —CH$_2$O— | C$_6$H$_5$ | |
| 151a | OCH$_3$ | CH$_3$ | —CH$_2$O— | C$_6$H$_5$ | |
| 152a | CH$_3$ | OCH$_3$ | —OCH$_2$— | C$_6$H$_5$ | |
| 153a | OCH$_3$ | CH$_3$ | —OCH$_2$— | C$_6$H$_5$ | |
| 154a | CH$_3$ | OCH$_3$ | —CO—OCH$_2$— | C$_6$H$_5$ | |
| 155a | OCH$_3$ | CH$_3$ | —CO—OCH$_2$— | C$_6$H$_5$ | |
| 156a | CH$_3$ | OCH$_3$ | —CO—OCH$_2$— | 1-methylcyclopropyl | |
| 157a | OCH$_3$ | CH$_3$ | —CO—OCH$_2$— | 1-methylcyclopropyl | |
| 158a | C$_2$H$_5$ | OCH$_3$ | —CH=CH— | C$_6$H$_5$ | |
| 159a | OCH$_3$ | C$_2$H$_5$ | —CH=CH— | C$_6$H$_5$ | |
| 160a | C$_2$H$_5$ | OCH$_3$ | —CH$_2$CH$_2$— | C$_6$H$_5$ | |
| 161a | OCH$_3$ | C$_2$H$_5$ | —CH$_2$CH$_2$— | C$_6$H$_5$ | |
| 162a | C$_2$H$_5$ | OCH$_3$ | —CH$_2$O— | C$_6$H$_5$ | |
| 163a | OCH$_3$ | C$_2$H$_5$ | —CH$_2$O— | C$_6$H$_5$ | |
| 164a | C$_2$H$_5$ | OCH$_3$ | —OCH$_2$— | C$_6$H$_5$ | |
| 165a | OCH$_3$ | C$_2$H$_5$ | —OCH$_2$— | C$_6$H$_5$ | |
| 166a | C$_2$H$_5$ | OCH$_3$ | —CO—OCH$_2$— | C$_6$H$_5$ | |
| 167a | OCH$_3$ | C$_2$H$_5$ | —CO—OCH$_2$— | C$_6$H$_5$ | |
| 168a | C$_2$H$_5$ | OCH$_3$ | —CO—OCH$_2$— | 1-methylcyclopropyl | |
| 169a | OCH$_3$ | C$_2$H$_5$ | —CO—OCH$_2$— | 1-methylcyclopropyl | |
| 170a | CH$_3$ | SCH$_3$ | —CH=CH— | C$_6$H$_5$ | |
| 171a | SCH$_3$ | CH$_3$ | —CH=CH— | C$_6$H$_5$ | |
| 172a | CH$_3$ | SCH$_3$ | —CH$_2$CH$_2$— | C$_6$H$_5$ | |
| 173a | SCH$_3$ | CH$_3$ | —CH$_2$CH$_2$— | C$_6$H$_5$ | |
| 174a | CH$_3$ | SCH$_3$ | —CH$_2$O— | C$_6$H$_5$ | |
| 175a | SCH$_3$ | CH$_3$ | —CH$_2$O— | C$_6$H$_5$ | |
| 176a | CH$_3$ | SCH$_3$ | —OCH$_2$— | C$_6$H$_5$ | |
| 177a | SCH$_3$ | CH$_3$ | —OCH$_2$— | C$_6$H$_5$ | |
| 178a | CH$_3$ | SCH$_3$ | —CO—OCH$_2$— | C$_6$H$_5$ | |
| 179a | SCH$_3$ | CH$_3$ | —CO—OCH$_2$— | C$_6$H$_5$ | |
| 180a | CH$_3$ | SCH$_3$ | —CO—OCH$_2$— | 1-methylcyclopropyl | |
| 181a | SCH$_3$ | CH$_3$ | —CO—OCH$_2$— | 1-methylcyclopropyl | |
| 182a | C$_2$H$_5$ | SCH$_3$ | —CH=CH— | C$_6$H$_5$ | |
| 183a | SCH$_3$ | C$_2$H$_5$ | —CH=CH— | C$_6$H$_5$ | |
| 184a | C$_2$H$_5$ | SCH$_3$ | —CH$_2$CH$_2$— | C$_6$H$_5$ | |
| 185a | SCH$_3$ | C$_2$H$_5$ | —CH$_2$CH$_2$— | C$_6$H$_5$ | |
| 186a | C$_2$H$_5$ | SCH$_3$ | —CH$_2$O— | C$_6$H$_5$ | |
| 187a | SCH$_3$ | C$_2$H$_5$ | —CH$_2$O— | C$_6$H$_5$ | |
| 188a | C$_2$H$_5$ | SCH$_3$ | —OCH$_2$— | C$_6$H$_5$ | |
| 189a | SCH$_3$ | C$_2$H$_5$ | —OCH$_3$— | C$_6$H$_5$ | |
| 190a | C$_2$H$_5$ | SCH$_3$ | —CO—OCH$_2$— | C$_6$H$_5$ | |
| 191a | SCH$_3$ | C$_2$H$_5$ | —CO—OCH$_2$— | C$_6$H$_5$ | |
| 192a | C$_2$H$_5$ | SCH$_3$ | —CO—OCH$_2$— | 1-methylcyclopropyl | |
| 193a | SCH$_3$ | C$_2$H$_5$ | —CO—OCH$_2$— | 1-methylcyclopropyl | |
| 194a | CH$_3$ | oxiranyl (CH—CH$_2$ with O bridge) | —CH=CH— | C$_6$H$_5$ | |
| 195a | oxiranyl (CH—CH$_2$ with O bridge) | CH$_3$ | —CH=CH— | C$_6$H$_5$ | |
| 196a | CH$_3$ | oxiranyl (CH—CH$_2$ with O bridge) | —CH$_2$CH$_2$— | C$_6$H$_5$ | |

TABLE 2-continued (structure with $X_n$ on benzene ring, Z-Y substituent, CH$_3$OOC-C=C-R$^1$/R$^2$) (X = hydrogen)

| No. | R$^1$ | R$^2$ | Y | Z | Data |
|---|---|---|---|---|---|
| 197a | oxiranyl (CH—CH$_2$ with O) | CH$_3$ | —CH$_2$CH$_2$— | C$_6$H$_5$ | |
| 198a | CH$_3$ | oxiranyl | —CH$_2$O— | C$_6$H$_5$ | |
| 199a | oxiranyl | CH$_3$ | —CH$_2$O— | C$_6$H$_5$ | |
| 200a | CH$_3$ | oxiranyl | —OCH$_2$— | C$_6$H$_5$ | |
| 201a | oxiranyl | CH$_3$ | —OCH$_2$— | C$_6$H$_5$ | |
| 202a | CH$_3$ | oxiranyl | —CO—OCH$_2$— | C$_6$H$_5$ | |
| 203a | oxiranyl | CH$_3$ | —CO—OCH$_2$— | C$_6$H$_5$ | |
| 204a | CH$_3$ | oxiranyl | —CO—OCH$_2$— | 1-methylcyclopropyl | |
| 205a | oxiranyl | CH$_3$ | —CO—OCH$_2$— | 1-methylcyclopropyl | |

TABLE 3

(structure with $X_n$ on benzene ring, Z-Y substituent, CH$_3$OOC-C=C-R$^1$/R$^2$) (X = hydrogen)

| No. | R$^1$ R$^2$ | Y | Z | Data |
|---|---|---|---|---|
| 1b | —(CH$_2$)$_3$— | —CH=CH— | C$_6$H$_5$ | |
| 2b | —(CH$_2$)$_3$— | —CH$_2$CH$_2$ | C$_6$H$_5$ | |
| 3b | —(CH$_2$)$_3$— | —CH$_2$O— | C$_6$H$_5$ | |
| 4b | —(CH$_2$)$_3$— | —O—CH$_2$— | C$_6$H$_5$ | |
| 5b | —(CH$_2$)$_3$— | —CO—OCH$_2$— | C$_6$H$_5$ | |
| 6b | —(CH$_3$)$_3$— | —CO—OCH$_2$— | 1-methylcyclopropyl | |
| 7b | —(CH$_2$)$_4$— | —CH=CH— | C$_6$H$_5$ | |
| 8b | —(CH$_2$)$_4$— | —CH$_2$CH$_2$— | C$_6$H$_5$ | |
| 9b | —(CH$_2$)$_4$— | —CH$_2$O— | C$_6$H$_5$ | |
| 10b | —(CH$_2$)$_4$— | —OCH$_2$— | C$_6$H$_5$ | |
| 11b | —(CH$_2$)$_4$— | —CO—OCH$_2$— | C$_6$H$_5$ | |
| 12b | —(CH$_2$)$_4$— | —CO—OCH$_2$— | 1-methylcyclopropyl | |
| 13b | —(CH$_2$)$_5$— | —CH=CH— | C$_6$H$_5$ | |
| 14b | —(CH$_2$)$_5$— | —CH$_2$CH$_2$— | C$_6$H$_5$ | |
| 15b | —(CH$_2$)$_5$— | —CH$_2$O— | C$_6$H$_5$ | |
| 16b | —(CH$_2$)$_5$— | —OCH$_2$— | C$_6$H$_5$ | |
| 17b | —(CH$_2$)$_5$— | —CO—OCH$_2$— | C$_6$H$_5$ | |

TABLE 3-continued $$\text{structure: phenyl ring with } X_n \text{ substituent, } Z-Y- \text{ group, and } CH_3OOC-C=C(R^1)(R^2)$$

(X = hydrogen)

| No. | R¹ | R² | Y | Z | Data |
|---|---|---|---|---|---|
| 18b | —(CH₂)₅— | | —CO—OCH₂— | 1-methylcyclopropyl | |
| 19b | —CH=CH—CH=CH— | | —CH=CH— | C₆H₅ | |
| 20b | —CH=CH—CH=CH— | | —CH₂CH₂— | C₆H₅ | |
| 21b | —CH=CH—CH=CH— | | —CH₂O— | C₆H₅ | |
| 22b | —CH=CH—CH=CH— | | —OCH₂— | C₆H₅ | |
| 23b | —CH=CH—CH=CH— | | —CO—OCH₂— | C₆H₅ | |
| 24b | —CH=CH—CH=CH— | | —CO—OCH₂— | 1-methylcyclopropyl | |
| 25b | —CH₂CH₂OCH₂CH₂— | | —CH=CH— | C₆H₅ | |
| 26b | —CH₂CH₂OCH₂CH₂— | | —CH₂CH₂— | C₆H₅ | |
| 27b | —CH₂CH₂OCH₂CH₂— | | —CH₂O— | C₆H₅ | |
| 28b | —CH₂CH₂OCH₂CH₂— | | —OCH₂— | C₆H₅ | |
| 29b | —CH₂CH₂OCH₂CH₂— | | —CO—OCH₂— | C₆H₅ | |
| 30b | —CH₂CH₂OCH₂CH₂— | | —CO—OCH₂— | 1-methylcyclopropyl | |
| 31b | —OCH₂CH₂O— | | —CH=CH— | C₆H₅ | |
| 32b | —OCH₂CH₂O— | | —CH₂CH₂— | C₆H₅ | |
| 33b | —OCH₂CH₂O— | | —CH₂O— | C₆H₅ | |
| 34b | —OCH₂CH₂O— | | —OCH₂— | C₆H₅ | |
| 35b | —OCH₂CH₂O— | | —CO—OCH₂— | C₆H₅ | |
| 36b | —OCH₂CH₂O— | | —CO—OCH₂— | 1-methylcyclopropyl | |
| 37b | —(CH₂)₃O— | | —CH=CH— | C₆H₅ | |
| 38b | —(CH₂)₃O— | | —CH₂CH₂— | C₆H₅ | |
| 39b | —(CH₂)₃O— | | —CH₂O— | C₆H₅ | |
| 40b | —(CH₂)₃O— | | —OCH₂— | C₆H₅ | |
| 41b | —(CH₂)₃O— | | —CO—OCH₂— | C₆H₅ | |
| 42b | —(CH₂)₃O— | | —CO—OCH₂— | 1-methylcyclopropyl | |
| 43b | —SCH₂CH₂S— | | —CH=CH— | C₆H₅ | |
| 44b | —SCH₂CH₂S— | | —CH₂CH₂— | C₆H₅ | |
| 45b | —SCH₂CH₂S— | | —CH₂O— | C₆H₅ | |
| 46b | —SCH₂CH₂S— | | —OCH₂— | C₆H₅ | |
| 47b | —SCH₂CH₂S— | | —CO—OCH₂— | C₆H₅ | |
| 48b | —SCH₂CH₂S— | | —CO—OCH₂— | 1-methylcyclopropyl | |
| 49b | —S(CH₂)₃S— | | —CH=CH— | C₆H₅ | |
| 50b | —S(CH₂)₃S— | | —CH₂CH₂— | C₆H₅ | |
| 51b | —S(CH₂)₃S— | | —CH₂O— | C₆H₅ | |
| 52b | —S(CH₂)₃S— | | —OCH₂— | C₆H₅ | |
| 53b | —S(CH₂)₃S— | | —CO—OCH₂— | C₆H₅ | |
| 54b | —S(CH₂)₃S— | | —CO—OCH₂— | 1-methylcyclopropyl | |
| 55b | —CH₂OCH₂CH₂— | | —CH=CH— | C₆H₅ | |
| 56b | —CH₂CH₂OCH₂— | | —CH=CH— | C₆H₅ | |
| 57b | —CH₂OCH₂CH₂— | | —CH₂CH₂— | C₆H₅ | |
| 58b | —CH₂CH₂OCH₂— | | —CH₂CH₂— | C₆H₅ | |
| 59b | —CH₂OCH₂CH₂— | | —CH₂O— | C₆H₅ | |
| 60b | —CH₂CH₂OCH₂— | | —CH₂O— | C₆H₅ | |
| 61b | —CH₂OCH₂CH₂— | | —OCH₂— | C₆H₅ | |
| 62b | —CH₂CH₂OCH₂— | | —OCH₂— | C₆H₅ | |
| 63b | —CH₂OCH₂CH₂— | | —CO—OCH₂— | C₆H₅ | |
| 64b | —CH₂CH₂OCH₂— | | —CO—OCH₂— | C₆H₅ | |
| 65b | —CH₂OCH₂CH₂— | | —CO—OCH₂— | 1-methylcyclopropyl | |
| 66b | —CH₂CH₂OCH₂— | | —CO—OCH₂— | 1-methylcyclopropyl | |
| 67b | —COOCH₂CH₂— | | —CH=CH— | C₆H₅ | |
| 68b | —CH₂CH₂OCO— | | —CH=CH— | C₆H₅ | |
| 69b | —COOCH₂CH₂— | | —CH₂CH₂— | C₆H₅ | |
| 70b | —CH₂CH₂OCO— | | —CH₂CH₂— | C₆H₅ | |
| 71b | —COOCH₂CH₂— | | —CH₂O— | C₆H₅ | |
| 72b | —CH₂CH₂OCO— | | —CH₂O— | C₆H₅ | |
| 73b | —COOCH₂CH₂— | | —OCH₂— | C₆H₅ | |
| 74b | —CH₂CH₂OCO— | | —OCH₂— | C₆H₅ | |
| 75b | —COOCH₂CH₂— | | —CO—OCH₂— | C₆H₅ | |
| 76b | —CH₂CH₂OCO— | | —CO—OCH₂— | C₆H₅ | |
| 77b | —COOCH₂CH₂— | | —CO—OCH₂— | 1-methylcyclopropyl | |
| 78b | —CH₂CH₂OCO— | | —CO—OCH₂— | 1-methylcyclopropyl | |

In general terms, the novel compounds are extremely effective on a broad spectrum of phytopathogenic fungi, in particular those from the Ascomycetes and Basidiomycetes classes. Some of them have a systemic action and can be used as foliar and soil fungicides.

The fungicidal compounds are of particular interest for controlling a large number of fungi in various crops or their seeds, especially wheat, rye, barley, oats, rice, Indian corn, lawns, cotton, soybeans, coffee, sugar cane, fruit and ornamentals in horticulture and viticulture, and in vegetables such as cucumbers, beans and cucurbits.

The novel compounds are particularly useful for controlling the following plant diseases:

Erysiphe graminis in cereals,
Erysiphe cichoracearum and Sphaerotheca fuliginea in cucurbits.
Podosphaera leucotricha in apples,
Uncinula necator in vines,
Puccinia species in cereals,
Rhizoctonia species in cotton and lawns,
Ustilago species in cereals and sugarcane,
Venturia inaequalis (scab) in apples,
Helminthosporium species in cereals,
Septoria nodorum in wheat,
Botrytis cinerea (gray mold) in strawberries and grapes,
Cercospora arachidicola in groundnuts,
Pseudocercosporella herpotrichoides in wheat and barley,
Pyricularia oryzae in rice,
Phytophthora infestans in potatoes and tomatoes,
Fusarium and Verticillium species in various plants,
Plasmopara viticola in grapes,
Alternaria species in fruit and vegetables.

The compounds are applied by spraying or dusting the plants with the active ingredients, or treating the seeds of the plants with the active ingredients. They may be applied before or after infection of the plants or seeds by the fungi.

The novel substances can be converted into conventional formulations such as solutions, emulsions, suspensions, dusts, powders, pastes and granules. The application forms depend entirely on the purposes for which they are intended; they should at all events ensure a fine and uniform distribution of the active ingredient. The formulations are produced in known manner, for example by extending the active ingredient with solvents and/or carriers, with or without the use of emulsifiers and dispersants; if water is used as solvent, it is also possible to employ other organic solvents as auxiliary solvents. Suitable auxiliaries for this purpose are solvents such as aromatics (e.g., xylene, chlorinated aromatics (e.g., chlorobenzenes), paraffins (e.g., crude oil fractions, alcohols (e.g., methanol, butanol, ketones (e.g., cyclohexanone, amines e.g., ethanolamine, dimethylformamide), and water; carriers such as ground natural minerals e.g., kaolins, aluminas, talc and chalk) and ground synthetic minerals e.g., highly disperse silica and silicates); emulsifiers such as nonionic and anionic emulsifiers (e.g., polyoxyethylene fatty alcohol ethers, alkyl sulfonates and aryl sulfonates); and dispersants such as lignin, sulfite waste liquors and methylcellulose.

The fungicidal agents generally contain from 0.1 to 95, and preferably from 0.5 to 90, wt % of active ingredient. The application rates are from 0.02 to 3 kg or more of active ingredient per hectare, depending on the type of effect desired. The novel compounds may also be used for protecting materials, e.g., against Paecilomyces variotii.

The agents and the ready-to-use formulations prepared from them, such as solutions, emulsions, suspensions, powders, dusts, pastes and granules, are applied in conventional manner, for example by spraying, atomizing, dusting, scattering, dressing or watering.

Examples of formulations are given below.

I. 90 parts by weight of compound no. 151 (Table 1) is mixed with 10 parts by weight of N-methyl-α-pyrrolidone. A mixture is obtained which is suitable for application in the form of very fine drops.

II. 20 parts by weight of compound no. 151 (Table 1) is dissolved in a mixture consisting of 80 parts by weight of xylene, 10 parts by weight of the adduct of 8 to 10 moles of ethylene oxide and 1 mole of oleic acid-N-monoethanolamide, 5 parts by weight of the calcium salt of dodecylbenzenesulfonic acid, and 5 parts by weight of the adduct of 40 moles of ethylene oxide and 1 mole of castor oil. By pouring the solution into water and uniformly distributing it therein, an aqueous dispersion is obtained.

III. 20 parts by weight of compound no. 151 is dissolved in a mixture consisting of 40 parts by weight of cyclohexanone, 30 parts by weight of isobutanol, 20 parts by weight of the adduct of 40 moles of ethylene oxide and 1 mole of castor oil. By pouring the solution into water and finely distributing it therein, an aqueous dispersion is obtained.

IV. 20 parts by weight of compound no. 151 is dissolved in a mixture consisting of 25 parts by weight of cyclohexanol, 65 parts by weight of a mineral oil fraction having a boiling point between 210° and 280° C. and 10 parts by weight of the adduct of 40 moles of ethylene oxide and 1 mole of castor oil. By pouring the solution into water and uniformly distributing it therein, an aqueous dispersion is obtained.

V. 80 parts by weight of compound no. 151 is well mixed with 3 parts by weight of the sodium salt of diisobutylnaphthalene-α-sulfonic acid, 10 parts by weight of the sodium salt of a lignin-sulfonic acid obtained from a sulfate waste liquor, and 7 parts by weight of powdered silica gel, and triturated in a hammer mill. By uniformly distributing the mixture in water, a spray liquor is obtained.

VI. 3 parts by weight of compound no. 151 is intimately mixed with 97 parts by weight of particulate kaolin. A dust is obtained containing 3% by weight of the active ingredient.

VII. 30 parts by weight of compound no. 151 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound no. 151 is intimately mixed with 10 parts of the sodium salt of a phenolsulfonic acid-urea-formaldehyde condensate, 2 parts of silica gel and 48 parts of water to give a stable aqueous dispersion. Dilution in water gives an aqueous dispersion.

IX. 20 parts by weight of compound no. 151 is intimately mixed with 2 parts by weight of the calcium salt of dodecylbenzenesulfonic acid, 8 parts by weight of a fatty alcohol polyglycol ether, 2 parts by weight of the sodium salt of a phenolsulfonic acid-urea-formaldehyde condensate and 68 parts by weight of a paraffinic mineral oil. A stable oily dispersion is obtained.

In these application forms, the agents according to the invention may also be present together with other active ingredients, for example herbicides, insecticides, growth regulators, and fungicides, and may furthermore be mixed and applied together with fertilizers. Admixture with other fungicides frequently results in an increase in the fungicidal spectrum.

The following list of fungicides with which the novel compounds may be combined is intended to illustrate possible combinations but not to impose any restrictions.

Examples of fungicides which may be combined with the novel compounds are:

sulfur,
dithiocarbamates and their derivatives, such as
ferric dimethyldithiocarbamate,
zinc dimethyldithiocarbamate,
zinc ethylenebisdithiocarbamate,
manganese ethylenebisdithiocarbamate,
manganese zinc ethylenediaminebisdithiocarbamate,
tetramethylthiuram disulfides,
ammonia complex of zinc N,N'-ethylenebisdithiocarbamate,
ammonia complex of zinc N,N'-propylenebisdithiocarbamate.
zinc N,N'-propylenebisdithiocarbamate and N,N'-polypropylenebis(thiocarbamyl) disulfide;
nitro derivatives, such as
dinitro(1-methylheptyl)-phenyl crotonate.
2-sec-butyl-4,6-dinitrophenyl 3,3-dimethylacrylate,
2-sec-butyl-4,6-dinitrophenyl isopropylcarbonate and diisopropyl 5-nitroisophthalate;
heterocyclic substances, such as
2-heptadecylimidazol-2-yl acetate,
2,4-dichloro-6-(o-chloroanilino)-s-triazine,
O,O-diethyl phthalimidophosphonothioate,
5-amino-1[-bis-(dimethylamino)]-3-phosphinyl-1,2,4-troiazole,
2,3-dicyano-1,4-dithioanthraquinone,
2-thio-1,3-dithio[4,5-b]quinoxaline,
methyl 1-(butylcarbamyl)-2-benzimidazolecarbamate,
2-methoxycarbonylaminobenzimidazole,
2-fur-2-yl-benzimidazole,
2-thiazol-4-yl)benzimidazole,
N-(1,1,2,2-tetrachloroethylthio)-tetrahydrophthalimide.
N-trichloromethylthiotetrahydrophthalimide,
N-trichloromethylthiophthalimide,
N-dichlorofluoromethylthlo-N',N'-dimethyl-N-phenyl-sulfuric acid diamide,
5-ethoxy-3-trichloromethyl-1,2,3-thiadiazole,
2-thiocyanatomethylthlobenzothiazole.
1,4-dichloro-2,5-dimethoxybenzene,
4-(2-chlorophenylhydrazono)-3-methyl-5-isoxazolone.
2-thiopyridine 1-oxide.
8-hydroxyquinoline and its copper salt.
2,3-dihydro-5-carboxanilido-6-methyl-1,4-oxathiyne,
2,3-dihydro-5-carboxanilido-6-methyl-1,4-oxathiyne 4,4-dioxide,
2-methylfuran-3-carboxanilide.
2,5-dimethylfuran-3-carboxanilide,
2,4,5-trimethylfuran-3-carboxanilide,
2,5-dimethyl-N-cyclohexylfuran-3-carboxamide,
N-cyclohexyl-N-methoxy-2,5-diethylfuran-3-carboxamide,
2-methylbenzanilide,
2-iodobenzanilide,
N-formyl-N-morpholine-2,2,2-trichloroethylacetal,
piperazine-1,4-diylbis-(1-(2,2,2-trichloroethyl-formamide),
1-(3,4-dichloroanilino)-1-formylamino-2,2,2-trichloroethane.
2,6-dimethyl-N-tridecylmorpholine and its salts,
2,6-dimethyl-N-cylododecylmorpholine and its salts,
N-[3-(p-tert.-butylphenyl)-2-methylpropyl]-cis-2,6-dmethylmorpholine,
N-[3-(p-tert.-butylphenyl)-2-methylpropyl]-piperidine.
1-[2-(2,4-dichlorophenyl)-4-ethyl-1,3-dioxolan-2-ylethyl]-1H-1,2,4-triazole,
1-[2-(2,4-dichlorophenyl)-4-n-propyl-1,3-dioxolan-2-ylethyl]-1H-1,2,4-triazole,
N-(n-propyl)-N-(2,4,6-trichlorophenoxyethyl)-N'-imidazolyl-urea,
1-(4-chlorophenoxy)-3,3-dimethyl-1-(1H-1,2,4-triazol-1-yl)-butan-2-one.
1-(4-chlorophenoxy)-3,3-dimethyl-1-(1H-1,2,4-triazol-1-yl)-butan-2-ol,
1-(4-phenylphenoxy)-3,3-dimethyl-1-(1H-1,2,4-triazol-1-yl)-2-butanol,
α-(2-chlorophenyl)-α(4-chlorophenyl)-5-pyrimidinemethanol,
5-butyl-(2-dimethylamino-4-hydroxy-6-methylpyrimidine,
bis-(p-chlorophenyl)-3-pyridinemethanol,
1,2-bis-(3-ethoxycarbonyl-2-thioureido)-benzene.
1,2-bis-(3-methoxycarbonyl-2-thioureido)-benzene,
and various fungicides, such as dodecylguanidine acetate,
3-[3-(3,5-dimethyl-2-oxycyclohexyl)-2-hydroxyethyl]-glutaramide,
hexachlorobenzene,
DL-methyl-N-(2,6-dimethylphenyl)-N-fur-2-yl alanate,
methyl DL-N-(2,6-dimethylphenyl)-N-(2'-methoxyacetyl)-alanate,
N-(2,6-dimethylphenyl)-N-chloroacetyl-DL-2-aminobutyrolactone,
methyl DL-N-(2,6-dimethylphenyl)-N-(phenylacetyl)-alanate,
5-methyl-5-vinyl-3-(3,5-dichlorophenyl)-2,4-dioxo-1,3-oxazolidine,
3-[3,5-dichlorophenyl]-5-methyl-5-methoxymethyl-1,3-oxazolidine-2,4-dione,
3-(3,5-dichlorophenyl)-1-isopropylcarbamylhydantoin,
N-(3,5-dichlorophenyl)-1,2-dimethylcyclopropane-1,2-dicarboximide,
2-cyano-[N-ethylaminocarbonyl)-2-methoximino]-acetamide,
1-[2-(2,4-dichlorophenyl)-pentyl]-1H-1,2,4-triazole,
2,4-difluoro-α-(1H-1,2,4-triazole-1-ylmethyl)-benzhydryl alcohol,
N-(3-chloro-2,6-dinitro-4-trifluoromethylphenyl)-5-trifluoromethyl-3-chloro-2-aminopyridine, and
1-((bis-(4-fluorophenyl)-methylsilyl)-methyl)-1H-1,2,4-triazole.

Use example

For comparison purposes, N-tridecyl-2,6-dimethylmorpholine (A) disclosed in DE 1,164,152 was used.

Use example

Action on *Pyricularia oryzae* (protective)

Leaves of potted rice seedlings of the "Bahia" variety were sprayed to runoff with aqueous emulsions consisting (dry basis) of 80% of active ingredient and 20% of emulsifier, and inoculated 24 hours later with an aqueous spore suspension of *Pyricularia oryzae*. The plants were then set up in climatic cabinets at 22° to 24° C. and a relative humidity of 95 to 99%. The spread of the disease was determined after 6 days.

The results show that active ingredient 151 (Table 1) has, when applied as a 0.05wt % spray liquor, a better fungicidal action (80%) than prior art comparative agent A (40%).

We claim:

1. Acrylates of the formula I

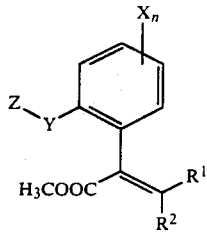
(I)

wherein

R$^1$ and R$^2$ are halogen or C$_{1-4}$-alkyl, C$_{1-3}$-alkoxy or C$_{1-3}$-alkylthio, where alkyl is unsubstituted or substituted by halogen, hydroxy, C$_{1-3}$-alkoxy, C$_{1-3}$-haloalkyl or C$_{1-3}$-haloalkoxy;

X is hydrogen, halogen, cyano, nitro, C$_1$-C$_4$-alkyl, C$_1$-C$_4$-alkoxy, halo-C$_1$-C$_4$-alkyl;

n is 1, 2, 3 or 4;

y is C$_1$-C$_4$-alkylene, C$_2$-C$_4$-alkenylene, C$_2$-C$_4$-alkynylene, O, unsubstituted or C$_1$-C$_4$-alkyl-substituted N, oxy-C$_1$-C$_4$-alkylene, thio-C$_1$-C$_4$-alkylene, —NCOO—, methyleneoxy or methylenethio; and Z is hydrogen, alkyl, cycloalkyl, aryl, aralkyl, aralkenyl, aralkoxy, aryloxy, aryloxyalkyl, alkoxy, alkoxyalkyl, alkylthio, or haloalkyl, these radicals being unsubstituted or substituted by halogen, cyano, nitro, alkyl, alkenyl, haloalkenyl, alkoxy, haloalkyl, alkoxycarbonyl or phenyl;

with the proviso that R$^1$ and R$^2$ cannot both be methyl, when X is hydrogen, Y is methylene, and Z is hydrogen, simultaneously.

2. A compound of the formula I as set forth in claim 1, where R$^1$ is methyl, R$^2$ is methyl, y is —CH$_2$O— and Z is 2—CH$_3$—C$_6$H$_4$.

3. A process for combating fungi, wherein the fungi, or the materials, plants, seed or the soil to be protected against fungus attack are treated with a fungicidally effective amount of a compound of the formula I

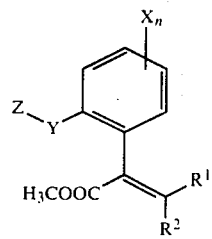
(I)

wherein

R$^1$ and R$^2$ are halogen or C$_{1-4}$-alkyl, C$_{1-3}$-alkoxy or C$_{1-3}$-alkylthio, where alkyl is unsubstituted or substituted by halogen, hydroxy, C$_{1-3}$-alkoxy, C$_{1-3}$-haloalkyl or C$_{1-3}$-haloalkoxy;

X is hydrogen, halogen, cyano, nitro, C$_1$-C$_4$-alkyl, C$_1$-C$_4$-alkoxy, halo-C$_1$-C$_4$alkyl;

n is 1, 2, 3 or 4;

Y is C$_1$-C$_4$-alkylene, C$_2$-C$_4$-alkenylene, C$_2$-C$_4$-alkynylene, O, unsubstituted or C$_1$-C$_4$-alkyl-substituted N, oxy-C$_1$-C$_4$-alkylene, thio-C$_1$-C$_4$-alkylene, —NCOO—, methyleneoxy or methylenethio; and Z is hydrogen, alkyl, cycloalkyl, aryl, aralkyl, aralkenyl, aralkoxy, aryloxy, aryloxyalkyl, alkoxy, alkoxyalkyl, alkylthio, or haloalkyl, these radicals being unsubstituted or substituted by halogen, cyano, nitro, alkyl, alkenyl, haloalkenyl, alkoxy, haloalkyl, alkoxycarbonyl or phenyl.

4. A fungicide containing an inert carrier and a fungicidally effective amount of a compound of the formula I

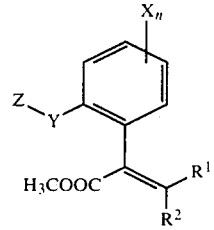
(I)

wherein

R$^1$ and R$^2$ are halogen or C$_{1-4}$-alkyl, C$_{1-3}$-alkoxy or C$_{1-3}$-alkylthio, where alkyl is unsubstituted or substituted by halogen, hydroxy, C$_{1-3}$-alkoxy, C$_{1-3}$-haloalkyl, or C$_{1-3}$-haloalkoxy;

X is hydrogen, halogen, cyano, nitro, C$_1$-C$_4$-alkyl, C$_1$-C$_4$-alkoxy, halo-C$_1$-C$_4$-alkyl;

n is 1, 2, 3 or 4;

y is C$_1$-C$_4$-alkylene, C$_2$-C$_4$-alkenylene, C$_2$-C$_4$-alkynylene, O, unsubstituted or C$_1$-C$_4$-alkyl-substituted N, oxy-C$_1$-C$_4$-alkylene, thio-C$_1$-C$_4$-alkylene, —NCOO—, methyleneoxy or methylenethio; and Z is hydrogen, alkyl, cycloalkyl, aryl, aralkyl, aralkenyl, aralkoxy, aryloxy, aryloxyalkyl, alkoxy, alkoxyalkyl, alkylthio, or haloalkyl, these radicals being unsubstituted or substituted by halogen, cyano, nitro, alkyl, alkenyl, haloalkenyl, alkoxy, haloalkyl, alkoxycarbonyl or phenyl.

* * * * *

UNITED STATES PATENT AND TRADEMARK OFFICE
CERTIFICATE OF CORRECTION

PATENT NO.  : 5,003,101
DATED       : March 26, 1991
INVENTOR(S) : Siegbert Brand et al.

It is certified that error appears in the above-identified patent and that said Letters Patent is hereby corrected as shown below:

On the title page item [75] Inventors:

The last inventor's name is spelled incorrectly, please delete "Gissela Lorenz" and insert -- Gisela Lorenz--

Signed and Sealed this

Eleventh Day of August, 1992

Attest:

DOUGLAS B. COMER

*Attesting Officer*    Acting Commissioner of Patents and Trademarks